(12) United States Patent
Su et al.

(10) Patent No.: US 11,872,315 B2
(45) Date of Patent: *Jan. 16, 2024

(54) METHOD FOR BLOOD PLASMA PROTEIN ACTIVITY PRESERVATION

(71) Applicant: Chung Chin Sun, Taipei (TW)

(72) Inventors: Cheng-Yao Su, Taipei (TW); Chung Chin Sun, Taipei (TW); Shan Shue Wang, Taipei (TW)

(73) Assignee: SUN, CHUNG CHIN, Taipei (TW)

( * ) Notice: Subject to any disclaimer, the term of this patent is extended or adjusted under 35 U.S.C. 154(b) by 604 days.

This patent is subject to a terminal disclaimer.

(21) Appl. No.: 16/472,111

(22) PCT Filed: Dec. 21, 2016

(86) PCT No.: PCT/CN2016/111228
§ 371 (c)(1),
(2) Date: Jun. 20, 2019

(87) PCT Pub. No.: WO2018/112780
PCT Pub. Date: Jun. 28, 2018

(65) Prior Publication Data
US 2020/0085747 A1 Mar. 19, 2020

(51) Int. Cl.
*A61K 9/19* (2006.01)
*A61K 35/16* (2015.01)

(52) U.S. Cl.
CPC ............ *A61K 9/19* (2013.01); *A61K 35/16* (2013.01)

(58) Field of Classification Search
None
See application file for complete search history.

(56) References Cited

U.S. PATENT DOCUMENTS

| 4,170,590 A * | 10/1979 | Stephan | C12Y 304/21005 424/530 |
|---|---|---|---|
| 4,812,310 A | 8/1989 | Sato et al. | |
| 5,330,974 A | 7/1994 | Pines et al. | |
| 8,486,617 B2 * | 7/2013 | Ho | A61P 13/12 435/2 |
| 9,669,076 B2 * | 6/2017 | Besman | A61K 47/26 |
| 2016/0215051 A1 * | 7/2016 | Sharma | A61P 43/00 |

FOREIGN PATENT DOCUMENTS

| CA | 2 796 729 A1 | 10/2011 |
| CN | 1399560 A | 2/2003 |
| CN | 103405754 A | 11/2013 |
| CN | 104231073 A | 12/2014 |

OTHER PUBLICATIONS

International Search Report for PCT/CN2016/111228 (PCT/ISA/210) dated Sep. 6, 2017.
Written Opinion of the International Searching Authority for PCT/CN2016/111228 (PCT/ISA/237) dated Sep. 6, 2017.

* cited by examiner

*Primary Examiner* — Nghi V Nguyen
(74) *Attorney, Agent, or Firm* — Birch, Stewart, Kolasch & Birch, LLP

(57) ABSTRACT

A method for blood plasma protein activity preservation is provided. The method comprises the steps of mixing blood plasma with two or more protectants selected from the group consisting of triglyceride, glycerol, propylene glycol, alanine, serine, glycine, alginate, and sucrose to obtain a mixture; and lyophilizing the mixture.

1 Claim, 23 Drawing Sheets

METHOD FOR BLOOD PLASMA PROTEIN ACTIVITY PRESERVATION

FIELD OF THE INVENTION

The present invention relates to a method for blood plasma protein activity preservation.

BACKGROUND OF THE INVENTION

Blood plasma is the pale yellow colored liquid component of blood that normally holds the blood cells in whole blood in suspension; this makes plasma the extracellular matrix of blood cells. It is mostly water and contains dissolved proteins (e.g., serum albumins, globulins, and fibrinogen), glucose, clotting factors, electrolytes, hormones, vitamins and carbon dioxide. Plasma plays a vital role in an intravascular osmotic effect that keeps electrolytes in balanced form and protects the body from infection and other blood disorders.

Blood plasma can be prepared by spinning a tube of fresh blood containing an anticoagulant in a centrifuge until the blood cells fall to the bottom of the tube. The use of blood plasma as a substitute for whole blood and for transfusion purposes was proposed in 1918. A dried plasma package for the armed forces was developed as it would reduce breakage and make the transportation, packaging, and storage much simpler. Serum albumin replaced dried plasma for combat use during the Korean War.

Plasma serves a variety of functions, from maintaining an appropriate blood pressure and volume to supplying critical proteins for blood clotting and immunity. It also serves as the medium for exchange of vital minerals such as sodium and potassium and helps to maintain a proper pH (acid-base) balance in the body, which is critical to cell function. Plasma as a blood product prepared from blood donations is used in blood transfusions, typically as Fresh Frozen Plasma (FFP) or Plasma Frozen within 24 hours after Phlebotomy (PF24). Plasma is frozen quickly after donation (up to 24 hours) to preserve clotting factors, stored up to one year, and thawed shortly before use. It is now usually used with thrombin in cases of excessive bleeding or to prevent bleeding in those patients with abnormal coagulation tests that are undergoing an invasive procedure. It is commonly transfused to trauma patients and patients with liver failure, severe infections, serious burns, or multiple clotting factor deficiencies. The use of FFP in hospital practice has risen by over 20% in the past few years and concern has been raised about the appropriateness of its clinical use.

The state of the art of plasma storage is to frozen plasma quickly within 24 hours after phlebotomy and store it typically as Fresh Frozen Plasma (FFP) up to one year. The FFP may be thawed shortly before use. However, such storage method has at least the following drawbacks: (1) plasma may not be stored for a long term unless it is frozen as FFP and stored in an ultra-low temperature refrigerator; and (2) the fibrinogen activity cannot be well maintained after thawing for use.

BRIEF SUMMARY OF THE INVENTION

The present invention provides a method for blood plasma protein activity preservation, comprising mixing blood plasma with two or more protectants selected from the group consisting of triglyceride, glycerol, propylene glycol, alanine, serine, glycine, alginate, and sucrose to obtain a mixture, and lyophilizing the mixture.

In certain embodiments of the present invention, the two or more protectants comprise a first protectant of glycerol, and a second protectant selected from the group consisting of triglyceride, alanine and serine.

In certain embodiments of the present invention, the two or more protectants comprise a first protectant of propylene glycol, and a second protectant selected from the group consisting of triglyceride, glycine, alginate and sucrose.

In certain embodiments of the present invention, the two or more protectants comprise glycerol, triglyceride and propylene glycol.

In certain embodiments of the present invention, the two or more protectants comprise glycerol, triglyceride and sucrose.

According to the present invention, the blood plasma may be further mixed, in the mixing step, with a protectant selected from the group consisting of dextran, albumin and gelatin.

It is to be understood that both the foregoing general description and the following detailed description are exemplary and explanatory only and are not restrictive of the invention.

BRIEF DESCRIPTION OF THE DRAWINGS

The foregoing summary, as well as the following detailed description of the invention, will be better understood when read in conjunction with the appended drawing. In the drawings:

FIG. 1A shows the levels of PDGF-AB, FIG. 1B shows the levels of TGF-β1, and FIG. 1C shows the levels of VEGF. Amount of protectant used based on the volume of the plasma: % means % (w/v). Control: plasma only. The difference between data shown in the same style of bar (plasma reconstituted after the same period (1 hour, 1 month, or 6 months) of time after lyophilization) with different letters is statistically significant ($P<0.05$).

FIG. 2A shows the levels of PDGF-AB, FIG. 2B shows the levels of TGF-β1, and FIG. 2C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant ($P<0.05$).

FIG. 3A shows the levels of PDGF-AB, FIG. 3B shows the levels of TGF-β1, and FIG. 3C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant ($P<0.05$).

FIG. 4A shows the levels of PDGF-AB, FIG. 4B shows the levels of TGF-β1, and FIG. 4C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant (P<0.05).

FIG. 5A shows the levels of PDGF-AB, FIG. 5B shows the levels of TGF-β1, and FIG. 5C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant (P<0.05).

FIG. 6A shows the levels of PDGF-AB, FIG. 6B shows the levels of TGF-β1, and FIG. 6C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant (P<0.05).

FIG. 7A shows the levels of PDGF-AB, FIG. 7B shows the levels of TGF-β1, and FIG. 7C shows the levels of VEGF. Amount of protectant used based on the volume of the plasma: % means % (v/v). Control: plasma only. The difference between data shown in the same style of bar (plasma reconstituted after the same period of time (1 hour, 1 month, or 6 months) after lyophilization) with different letters is statistically significant (P<0.05).

FIG. 8A shows the levels of PDGF-AB, FIG. 8B shows the levels of TGF-β1, and FIG. 8C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant (P<0.05).

FIG. 9A shows the levels of PDGF-AB, FIG. 9B shows the levels of TGF-β1, and FIG. 9C shows the levels of VEGF. Amount of protectant used based on the volume of the plasma: % means % (v/v). Control: plasma only. The difference between data shown in the same style of bar (plasma reconstituted after the same period of time (1 hour, 1 month, or 6 months) after lyophilization) with different letters is statistically significant (P<0.05).

FIG. 10A shows the levels of PDGF-AB, FIG. 10B shows the levels of TGF-β1, and FIG. 10C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant (P<0.05).

FIG. 11A shows the levels of PDGF-AB, FIG. 11B shows the levels of TGF-β1, and FIG. 11C shows the levels of VEGF. Amount of protectant used based on the volume of the plasma: % means % (w/v). Control: plasma only. The difference between data shown in the same style of bar (plasma reconstituted after the same period of time (1 hour, 1 month, or 6 months) after lyophilization) with different letters is statistically significant (P<0.05).

FIG. 12A shows the levels of PDGF-AB, FIG. 12B shows the levels of TGF-β1, and FIG. 12C shows the levels of VEGF. Amount of protectant used based on the volume of the plasma: % means % (v/v). Control: plasma only. The difference between data shown in the same style of bar (plasma reconstituted after the same period of time (1 hour, 1 month, or 6 months) after lyophilization) with different letters is statistically significant (P<0.05).

FIG. 13A shows the levels of PDGF-AB, FIG. 13B shows the levels of TGF-β1, and FIG. 13C shows the levels of VEGF. Amount of protectant used based on the volume of the plasma: % means % (v/v) for triglyceride, glycerol and propylene glycol, and means % (w/v) for other protectants. Control: plasma only. 1: 2% glycerol+2% Dextran; 2: 0.1% Triglyceride+2% Dextran; 3: 0.16% glycerol+3% Albumin; 4: 0.1% Triglyceride+2% Propylene glycol; 5: 0.1% Triglyceride+2% glycerol; 6: 0.8% Glycine+1.6% Dextran; 7: 1.6% Glycine+1.6% Propylene glycol; 8: 0.8% Propylene glycol+4% Alginate; 9: 0.4% Propylene glycol+2.4% Albumin; 10: 1.6% Dextran+1.0% Propylene glycol; 11: 1% glycerol+2% Alanine; 12: 0.6% glycerol+1.2% Serine; 13: 0.08% Propylene glycol+2% Sucrose; 14: 0.08% Dextran+3.2% Albumin; and 15: 0.8% Glycine+1% Trehalose. The difference between data shown in the same style of bar (plasma reconstituted after the same period of time (1 hour, 1 month, or 6 months) after lyophilization) with different letters is statistically significant (P<0.05).

FIG. 14A shows the levels of PDGF-AB, FIG. 14B shows the levels of TGF-β1, and FIG. 14C shows the levels of VEGF. Amount of protectant used based on the volume of the plasma: % means % (v/v) for triglyceride, glycerol and propylene glycol, and means % (w/v) for other protectants. Control: plasma only. 1: 4% Glutamic acid+0.4% Propylene glycol+0.04% Dextran; 2: 0.4% Triglyceride+4% glycerol+0.8% Dextran; 3: 0.1% Triglyceride+4% glycerol+0.3% Sucrose; 4: 1% Triglyceride+1.6% glycerol+0.8% Propylene glycol; 5: 0.4% Glutamic acid+0.4% Albumin+4% Gelatin; 6: 1% Glutamic acid+4% Albumin+0.8% Dextran; 7: 0.01% Triglyceride+4% Dextran+0.8% Albumin; 8: 0.04% Triglyceride+0.08% glycerol+4% Albumin; 9: 4% Triglyceride+0.4% glycerol+0.8% Glycine; 10: 3% Trehalose+4% Alginate+0.8% Dextran; 11: 0.1% Glutamic acid+1% Trehalose+4% Dextran; 12: 3% Glutamic acid+3% Trehalose+3% Alginate. The difference between data shown in the same style of bar (plasma reconstituted after the same period of time (1 hour, 1 month, or 6 months) after lyophilization) with different letters is statistically significant (P<0.05).

FIG. 15A shows the levels of PDGF-AB, FIG. 15B shows the levels of TGF-β1, and FIG. 15C shows the levels of VEGF. Amount of protectant used based on the volume of the plasma: % means % (v/v) for triglyceride, glycerol and propylene glycol, and means % (w/v) for other protectants. Control: plasma only. 1: 0.4% Albumin+0.8%

Figure 1A:
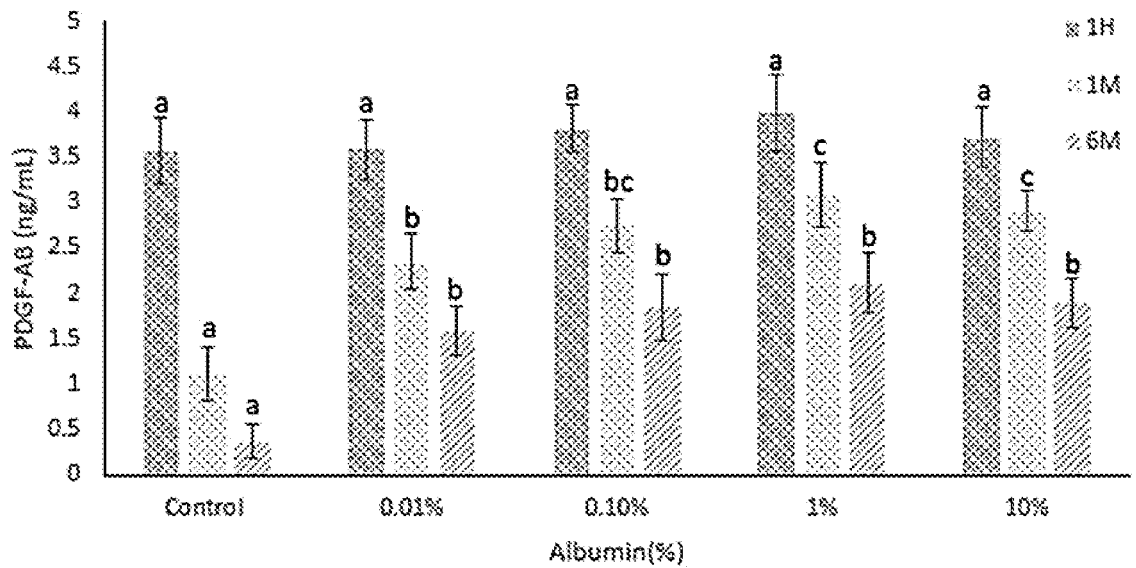
FIGS. 1A-1C show the growth factor levels in the plasma reconstituted from the plasma powder using albumin as a protectant.

Polyethylene glycol+4% glycerol+0.4% Glycine; 2: 1% Polyethylene glycol+0.4% Gelatin+0.4% Glutamic acid+ 0.4% Glucose; 3: 4% Triglyceride+0.4% Albumin+0.4% Dextran+0.4% glycerol; 4: 0.04% Triglyceride+0.4% Albumin+0.4% Polyethylene glycol+0.4% Glucose; 5: 0.01% Albumin+2% Dextran+0.4% serine+4% sucrose; 6: 0.04% Triglyceride+4% Albumin+0.4% Glycine+0.4% Trehalose; 7: 4% Albumin+0.4% Polyethylene glycol+0.4% Alanine+ 4% Trehalose; 8: 0.4% Triglyceride+4% Gelatin+0.4% Alginate+0.4% Glycine; 9: 2% Gelatin+2% Alginate+0.4% Glycine+0.4% Trehalose. The difference between data shown in the same style of bar (plasma reconstituted after the same period of time (1 hour, 1 month, or 6 months) after lyophilization) with different letters is statistically significant ($P<0.05$).

DETAILED DESCRIPTION OF THE INVENTION

The present invention provides a method for blood plasma protein activity preservation, comprising mixing blood plasma with two or more protectants selected from the group consisting of triglyceride, glycerol, propylene glycol, alanine, serine, glycine, alginate, and sucrose to obtain a mixture, and lyophilizing the mixture.

According to the present invention, the protectants may be added in the following amounts: (1) 0.01-10% (v/v) triglyceride based on the volume of the plasma, preferably 0.05-2% (v/v); (2) 0.01%-10% (v/v) glycerol based on the volume of the plasma, preferably 0.5-5% (v/v); (3) 0.01%-10% (v/v) propylene glycol based on the volume of the plasma, preferably 0.5-5% (v/v); (4) 0.01%-10% (w/v) alanine based on the volume of the plasma, preferably 0.5-5% (w/v); (5) 0.01%-10% (w/v) serine based on the volume of the plasma, preferably 0.05-5% (w/v); (6) 0.01%-10% (w/v) glycine based on the volume of the plasma, preferably 0.5-5% (w/v); (7) 0.01%-10% (w/v) alginate based on the volume of the plasma, preferably 0.5-10% (w/v); (8) 0.01%-10% (w/v) sucrose based on the volume of the plasma, preferably 0.5%-5% (w/v).

In certain embodiments of the present invention, the two or more protectants comprise a first protectant of glycerol, and a second protectant selected from the group consisting of triglyceride, alanine and serine. In some embodiments, the two or more protectants are glycerol and triglyceride. In some embodiments, the two or more protectants are glycerol and alanine. In some embodiments, the two or more protectants are glycerol and serine.

In certain embodiments of the present invention, the two or more protectants comprise a first protectant of propylene glycol, and a second protectant selected from the group consisting of triglyceride, glycine, alginate and sucrose. In some embodiments, the two or more protectants are propylene glycol and triglyceride. In some embodiments, the two or more protectants are propylene glycol and glycine. In some embodiments, the two or more protectants are propylene glycol and alginate. In some embodiments, the two or more protectants are propylene glycol and sucrose.

In certain embodiments of the present invention, the two or more protectants comprise glycerol, triglyceride and propylene glycol. In one embodiment, the two or more protectants are glycerol, triglyceride and propylene glycol. For example, the following amounts of protectants may be added (based on the volume of plasma): about 1% (v/v) triglyceride, about 1.6% (v/v) glycerol, and about 0.8% (v/v) propylene glycol.

In certain embodiments of the present invention, the two or more protectants comprise glycerol, triglyceride and sucrose. In one embodiment, the two or more protectants are glycerol, triglyceride and sucrose. For example, the following amounts of protectants may be added (based on the volume of plasma): about 0.1% (v/v) triglyceride, about 4% (v/v) glycerol, and about 2% (w/v) sucrose.

According to the present invention, the blood plasma may be further mixed, in the mixing step, with a protectant selected from the group consisting of dextran, albumin and gelatin.

The present invention is further illustrated by the following examples, which are provided for the purpose of demonstration rather than limitation.

Example 1: Blood Plasma Isolation

Whole blood were collected from volunteer donors must be performed by personal trained in phlebotomy/venipuncture using a double blood bag system (about 50 ml) (TerumoBCT, Japan) with anticoagulant (1 ml of Anticoagulant Citrate Dextrose (ACD) Solution Formula/per 10 ml of blood). After blood collection, gently mix the blood by inverting the tube several times to ensure thorough mixing with anticoagulant. For thorough mixing of blood collected into citrate tubes, it is recommended to invert the tube 3-4 times, while ACD tubes should be inverted eight times. Blood samples should be maintained at temperate conditions (20-24° C.) and centrifuged within 4 hours of blood collection. To separate the plasma, centrifuge the blood samples at 1200×g for 10 minutes at 22° C. If needed, RCF for a centrifuge can be calculated. After centrifugation, the plasma layer will be the upper layer of the separated blood and appear a clear, straw-yellow colored fluid.

Example 2: Plasma Lyophilized Powder Preparation

An appropriate amount of protectants was added to freshly collected plasma and mixed thoroughly to obtain a mixture. The mixture was then lyophilized to powder.

TABLE 1

| Amount of protectants used | |
| --- | --- |
| Protectants | Amount |
| Triglyceride | 0.01%-10% (v/v) |
| Glycerol | 0.01%-10% (v/v) |
| propylene glycol | 0.01%-10% (v/v) |
| Alanine | 0.1%-5% (w/v) |
| Serine | 0.01%-10% (w/v) |
| Glycine | 0.01%-10% (w/v) |
| Alginate | 0.01%-10% (w/v) |

Example 3: Fibrinogen Activity Examination 20 mg plasma powder one hour, one month and six months after lyophilization, respectively, was dissolved in 1 mL saline and mixed thoroughly. The reconstituted plasma was mixed with thrombin solution (35-45 IU/mL) at a ratio of 1:1 by volume. (1) Clotting Activity: Fibrinogen activity was examined by observing clotting formation and evaluated as excellent (+++), good (++), fair (+), or no activity (−). (2) Viscosity: The viscosity of thrombin-added plasma is considered as positively correlated to fibrinogen activity and as evaluated as excellent (+++), good (++), fair (+), or no viscosity (−). The results are shown in Tables 2-5 below.

TABLE 2

| | | One Hour | | One month | | Six months | |
|---|---|---|---|---|---|---|---|
| Protectants | Amount (based on the volume of the plasma; % means % (v/v) for triglyceride, glycerol and propylene glycol, and means % (w/v) for other protectants) | Clotting activity | Viscosity | Clotting activity | Viscosity | Clotting activity | Viscosity |
| | — (plasma only) | − | − | − | − | − | − |
| Ester - triglyceride | 0.01% (v/v) | + | + | + | − | − | − |
| | 0.1% (v/v) | + | + | − | − | − | − |
| | 1% (v/v) | + | + | − | − | − | − |
| | 10% (v/v) | + | + | − | − | − | − |
| Glycerol | 0.01% (v/v) | + | + | − | − | − | − |
| | 0.1% (v/v) | + | + | − | − | − | − |
| | 1% (v/v) | + | + | + | − | − | − |
| | 10% (v/v) | + | + | + | − | − | − |
| Amino Acid - glycine | 0.01% (w/v) | + | − | − | − | − | − |
| | 0.1% (w/v) | + | − | − | − | − | − |
| | 1% (w/v) | + | − | − | − | − | − |
| | 10% (w/v) | + | − | − | − | − | − |
| Amino Acid - alanine | 0.01% (w/v) | − | − | − | − | − | − |
| | 0.1% (w/v) | + | − | − | − | − | − |
| | 1% (w/v) | − | − | − | − | − | − |
| | 10% (w/v) | − | − | − | − | − | − |
| Amino Acid - glutamic acid | 0.01% (w/v) | + | − | − | − | − | − |
| | 0.1% (w/v) | + | − | − | − | − | − |
| | 1% (w/v) | + | + | − | − | − | − |
| | 10% (w/v) | + | − | − | − | − | − |
| Amino Acid - serine | 0.01% (w/v) | + | − | − | − | − | − |
| | 0.1% (w/v) | + | + | − | − | − | − |
| | 1% (w/v) | + | + | − | − | − | − |
| | 10% (w/v) | + | − | − | − | − | − |
| Albumin | 0.01% (w/v) | + | + | + | − | − | − |
| | 0.1% (w/v) | + | + | + | + | − | − |
| | 1% (w/v) | + | + | + | + | + | − |
| | 10% (w/v) | + | + | + | − | − | − |
| Gelatin | 0.01% (w/v) | + | + | + | − | − | − |
| | 0.1% (w/v) | + | + | + | + | − | − |
| | 1% (w/v) | + | + | + | + | + | − |
| | 10% (w/v) | + | + | + | − | − | − |
| Synthetic Polymer - propylene glycol | 0.01% (v/v) | + | + | + | − | − | − |
| | 0.1% (v/v) | + | + | + | − | − | − |
| | 1% (v/v) | + | + | + | + | − | − |
| | 10% (v/v) | + | + | + | + | − | − |
| Polysaccharide - dextran | 0.01% (w/v) | + | + | + | + | + | + |
| | 0.1% (w/v) | + | + | + | + | + | + |
| | 1% (w/v) | + | + | + | + | + | + |
| | 10% (w/v) | + | + | + | + | + | + |
| Polysaccharide - alginate | 0.01% (w/v) | + | − | − | − | − | − |
| | 0.1% (w/v) | + | − | − | − | − | − |
| | 1% (w/v) | + | + | − | − | − | − |
| | 10% (w/v) | + | + | − | − | − | − |
| Monosaccharide - glucose | 0.01% (w/v) | − | − | − | − | − | − |
| | 0.1% (w/v) | + | − | − | − | − | − |
| | 1% (w/v) | + | − | − | − | − | − |
| | 10% (w/v) | − | − | − | − | − | − |
| Disaccharide - trehalose | 0.01% (w/v) | − | − | − | − | − | − |
| | 0.1% (w/v) | + | − | − | − | − | − |
| | 1% (w/v) | + | − | − | − | − | − |
| | 10% (w/v) | + | − | − | − | − | − |
| Disaccharide - sucrose | 0.01% (w/v) | + | + | − | − | − | − |
| | 0.1% (w/v) | + | + | − | − | − | − |
| | 1% (w/v) | + | + | − | − | − | − |
| | 10% (w/v) | + | + | − | − | − | − |

TABLE 3

Fibrinogen activity (two protectants)

| Protectants/Amounts (based on the volume of the plasma; % means % (v/v) for triglyceride, glycerol and propylene glycol, and means % (w/v) for other protectants) | One Hour | | One month | | Six months | |
|---|---|---|---|---|---|---|
| | Clotting activity | Viscosity | Clotting activity | Viscosity | Clotting activity | Viscosity |
| — (plasma only) | − | − | − | − | − | − |
| 0.1% Triglyceride + 2% glycerol | ++ | ++ | + | + | + | − |
| 0.1% Triglyceride + 2% Glycine | + | + | − | − | − | − |
| 0.1% Triglyceride + 2% Glutamic acid | + | + | − | − | − | − |
| 0.1% Triglyceride + 2% Albumin | ++ | + | − | − | − | − |
| 0.1% Triglyceride + 2% Gelatin | ++ | ++ | − | − | − | − |
| 0.1% Triglyceride + 2% Propylene glycol | ++ | ++ | + | + | + | − |
| 0.1% Triglyceride + 2% Dextran | ++ | ++ | ++ | + | + | − |
| 0.1% Triglyceride + 2% Alginate | ++ | ++ | − | − | − | − |
| 0.1% Triglyceride + 1% glucose | + | + | − | − | − | − |
| 0.1% Triglyceride + 1% Trehalose | + | + | + | − | − | − |
| 1% glycerol + 2% Alanine | + | + | + | + | + | − |
| 0.6% glycerol + 1.2% Serine | + | + | + | + | + | − |
| 0.16% glycerol + 3% Albumin | ++ | ++ | ++ | + | + | − |
| 2% glycerol + 2% Dextran | ++ | ++ | ++ | ++ | + | + |
| 0.08% glycerol + 2% Gelatin | ++ | ++ | + | − | − | − |
| 1% glycerol + 2% Alginate | + | + | + | − | − | − |
| 0.6% glycerol + 2% sucrose | + | + | + | − | − | − |
| 0.8% Glycine + 1.6% Albumin | + | − | − | − | − | − |
| 1.6% Glycine + 2% Propylene glycol | + | + | + | + | + | + |
| 0.8% Glycine +1.6% Dextran | + | + | + | + | + | + |
| 0.8% Glycine + 1% Trehalose | + | + | + | − | − | − |
| 2% Propylene glycol + 4% Alginate | + | + | + | + | + | + |
| 3.2% Propylene glycol + 1% Gelatin | + | + | + | − | + | − |
| 0.4% Propylene glycol + 2.4% Albumin | + | + | + | + | + | + |
| 0.08% Propylene glycol + 2% Sucrose | + | + | + | + | + | − |
| 0.08% Dextran + 3.2% Albumin | + | + | + | + | + | − |
| 0.06% Dextran + 1.6% Gelatin | + | + | + | + | − | − |
| 1.6% Dextran + 1.0% Propylene glycol | + | + | + | + | + | + |
| 2% Dextran + 1% Trehalose | + | + | + | − | − | − |

TABLE 4

Fibrinogen activity (three protectants)

| Protectants/Amounts (based on the volume of the plasma; % means % (v/v) for triglyceride, glycerol and propylene glycol, and means % (w/v) for other protectants) | One Hour | | One month | | Six months | |
|---|---|---|---|---|---|---|
| | Clotting activity | Viscosity | Clotting activity | Viscosity | Clotting activity | Viscosity |
| — (plasma only) | − | − | − | − | − | − |
| 4% Triglyceride + 0.4% glycerol + 0.8% Glycine | ++ | ++ | ++ | + | + | − |
| 1% Triglyceride + 1.6% glycerol + 0.8% Propylene glycol | ++ | ++ | ++ | ++ | + | + |
| 0.4% Triglyceride + 4% glycerol + 0.8% Dextran | ++ | ++ | ++ | ++ | + | + |
| 0.1% Triglyceride + 4% glycerol + 2% Sucrose | ++ | ++ | ++ | ++ | + | + |
| 0.04% Triglyceride + 0.08% glycerol + 4% Albumin | ++ | ++ | + | + | + | + |
| 0.01% Triglyceride + 4% Dextran + 0.8% Albumin | ++ | ++ | + | + | + | + |
| 4% Glutamic acid + 2% Propylene glycol + 0.04% Dextran | ++ | ++ | ++ | ++ | ++ | ++ |
| 1% Glutamic acid + 4% Albumin + 0.8% Dextran | ++ | ++ | + | + | + | + |
| 0.4% Glutamic acid + 0.4% Albumin + 4% Gelatin | ++ | ++ | + | + | + | + |
| 0.3% Trehalose + 4% Alginate + 0.8% Dextran | ++ | ++ | + | + | + | − |

TABLE 4-continued

Fibrinogen activity (three protectants)

| Protectants/Amounts (based on the volume of the plasma; % means % (v/v) for triglyceride, glycerol and propylene glycol, and means % (w/v) for other protectants) | One Hour | | One month | | Six months | |
|---|---|---|---|---|---|---|
| | Clotting activity | Viscosity | Clotting activity | Viscosity | Clotting activity | Viscosity |
| 0.1% Glutamic acid + 1% Trehalose + 4% Dextran | + | + | + | + | + | − |
| 3% Glutamic acid + 1% Trehalose + 3% Alginate | ++ | ++ | − | − | − | − |

TABLE 5

Fibrinogen activity (four protectants)

| Protectants/Amounts (based on the volume of the plasma; % means % (v/v) for triglyceride, glycerol and propylene glycol, and means % (w/v) for other protectants) | One Hour | | One month | | Six months | |
|---|---|---|---|---|---|---|
| | Clotting activity | Viscosity | Clotting activity | Viscosity | Clotting activity | Viscosity |
| — (plasma only) | − | − | − | − | − | − |
| 4% Triglyceride + 0.4% Albumin + 0.4% Dextran + 4% glycerol | ++ | ++ | ++ | ++ | + | + |
| 0.4% Triglyceride + 4% Gelatin + 0.4% Alginate + 0.4% Glycine | ++ | ++ | ++ | + | − | − |
| 0.04% Triglyceride + 0.4% Albumin + 0.4% Polyethylene glycol + 1% Glucose | ++ | ++ | ++ | + | + | + |
| 0.04% Triglyceride + 4% Albumin + 0.4% Glycine + 1% Trehalose | ++ | ++ | + | + | + | − |
| 1% Polyethylene glycol + 0.4% Gelatin + 0.4% Glutamic acid + 1% Glucose | +++ | ++ | ++ | + | + | + |
| 0.01% Albumin + 2% Dextran + 0.4% serine + 2% sucrose | ++ | ++ | + | + | + | − |
| 2% Gelatin + 2% Alginate + 0.4% Glycine + 1% Trehalose | ++ | ++ | + | − | − | − |
| 4% Albumin + 0.4% Polyethylene glycol + 0.4% Alanine + 1% Trehalose | ++ | ++ | + | + | + | − |
| 0.4% Albumin + 0.8% Polyethylene glycol + 4% glycerol + 0.4% Glycine | +++ | +++ | +++ | ++ | + | + |

The protectants triglyceride, glycerol, propylene glycol, alanine, serine, glycine, alginate, and sucrose when used alone in the preparation of plasma lyophilized powder, are not able to preserve the fibrinogen activity for up to one month or six months. However, the fibrinogen activity may be preserved for up to one month or six months when these protectants are used in combination.

Example 4: Growth Factor Level Examination 20 mg plasma powder one hour, one month and six months after lyophilization, respectively, was dissolved in 1 mL saline and mixed thoroughly. The samples were analyzed within 1 hour after reconstitution by commercially available immunoassays. Standards and samples were assayed in triplicate, and mean values were calculated. The results were multiplied by the dilution factor applied to the samples.

PDGF-AB, TGF-β1, and VEGF levels were measured by ELISA assay.

1. PDGF-AB: PDGF-AB level was assayed using DueSet® ELISA kits (#DY222, R&D Systems, Minneapolis, Minn.). Samples were diluted 20 times in the Reagent Diluent. The plates were incubated for 2 hours, washed, and incubated with enzyme conjugated antibodies to PDGF-AB for an additional 2 hours at room temperature. The wells were washed using the Wash Buffer, then the Substrate Solution was added for 20 minutes at room temperature. Wells were protected from light. Stop Solution was added to each well, and the absorptions at 450 nm were determined using a microplate reader (Gen5, Biotek, VT, USA). The range detectable dose was 15.6-1000 pg/ml.

2. TGF-β1: TGF-β1 level was determined by DueSet® ELISA kits (#DY240, R&D Systems). Samples were diluted 20-fold in the Reagent Diluent. A dilution series of TGF-β1 standards was prepared in 100-μl volumes in 96-well microliter plates coated with TGF-β-receptor II. Before analysis of TGF-β1, acid activation and neutralization was performed to activate latent TGF-β1 to the immunoreactive form. For this purpose, 0.5 ml samples were mixed with 0.1 ml of 1N HCl, incubated at room temperature for 10 minutes, neutralized by an addition of 0.1 ml of 1.2N NaOH/0.5M HEPES (N-[2-hydroxyethyl] piperazine-N0-[2-ethanesulfonic acid]) from Sigma (H-7523), and centrifuged. The supernatant fraction was then assayed for total TGF-β1 content. Aliquots (50 μl) were applied in duplicate to the microliter plate, which was then covered and incubated for 2 h at room temperature. The wells were then washed, enzyme-conjugated polyclonal antibody to TGF-b1 was added, and incubation continued for 2 h at room temperature. Measurements were completed as described above. The range detection limit of TGF-β1 was 31.20-2000 pg/ml.

3. VEGF: VEGF level was assayed using DueSet® ELISA kits (#DY293B, R&D Systems, Minneapolis, Minn.). Samples were diluted 2-fold in Reagent Diluent. The range detectable dose is typically less than 31.2-2000 pg/ml. 100 μl of assay reagent diluent were added to each well, followed by 100 μl of standard (VEGF standard). The plates were covered with adhesives strips and incubated for 2 h at room temperature. The wells were washed 4 times and then incubated with enzyme-conjugated VEGF for 2 h at room temperature. Measurements were completed as described above.

Figure 1B:
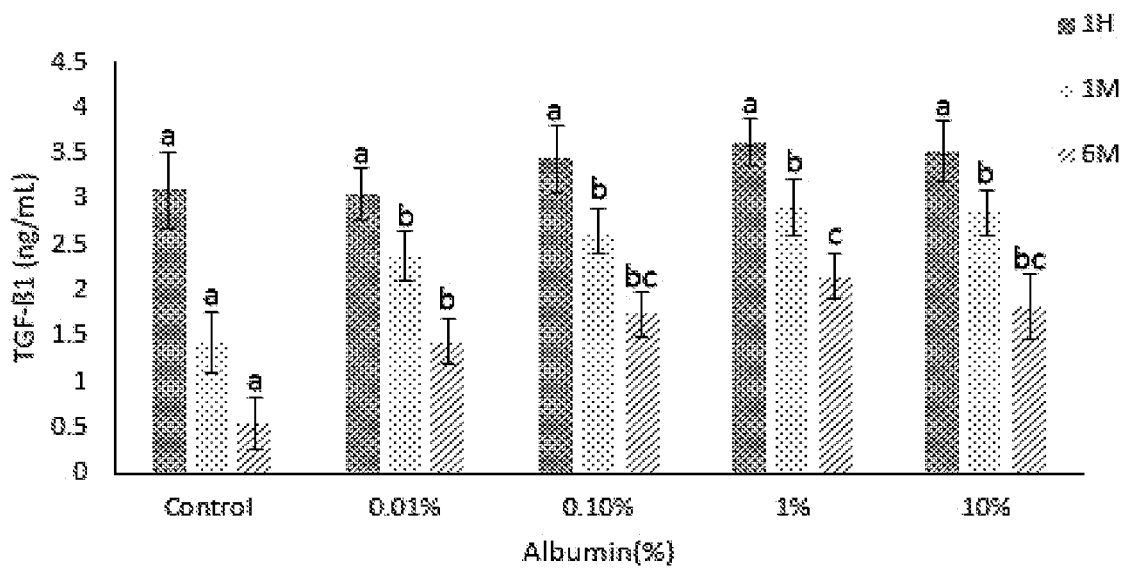
Figure 1C:
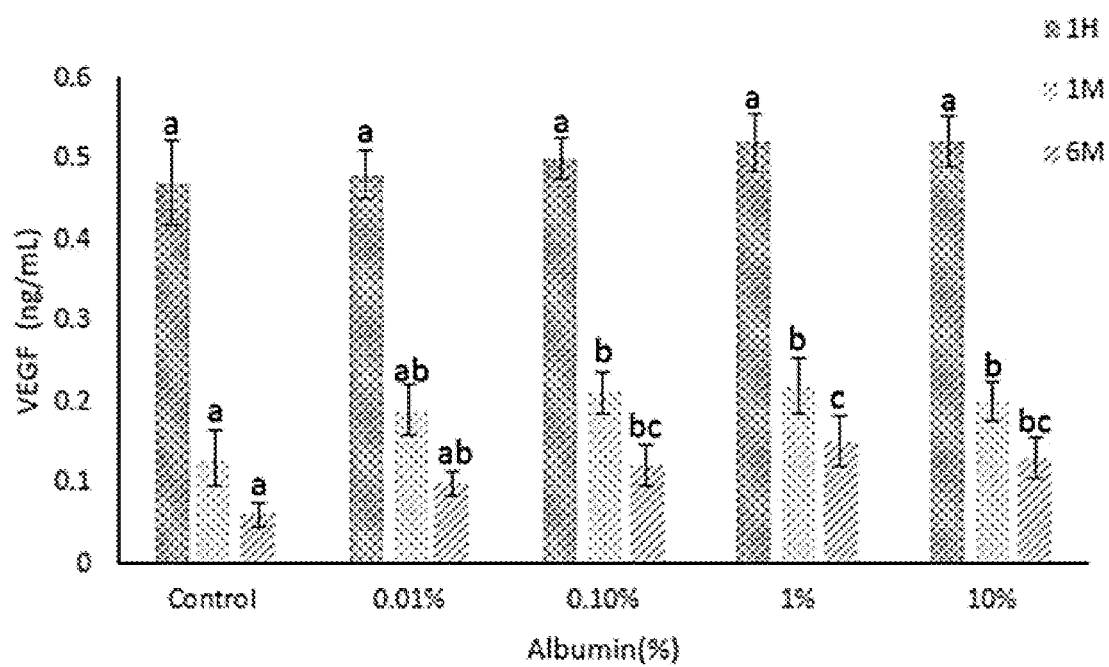
Figure 2A:
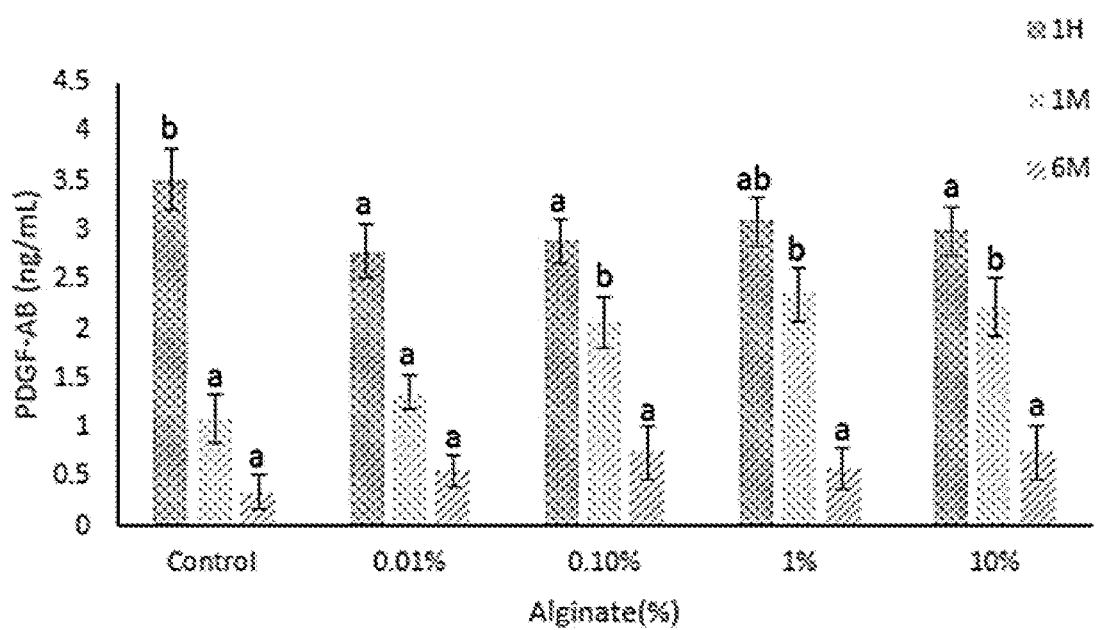
FIGS. 2A-2C show the growth factor levels in the plasma reconstituted from the plasma powder using alginate as a protectant.
Figure 2B:
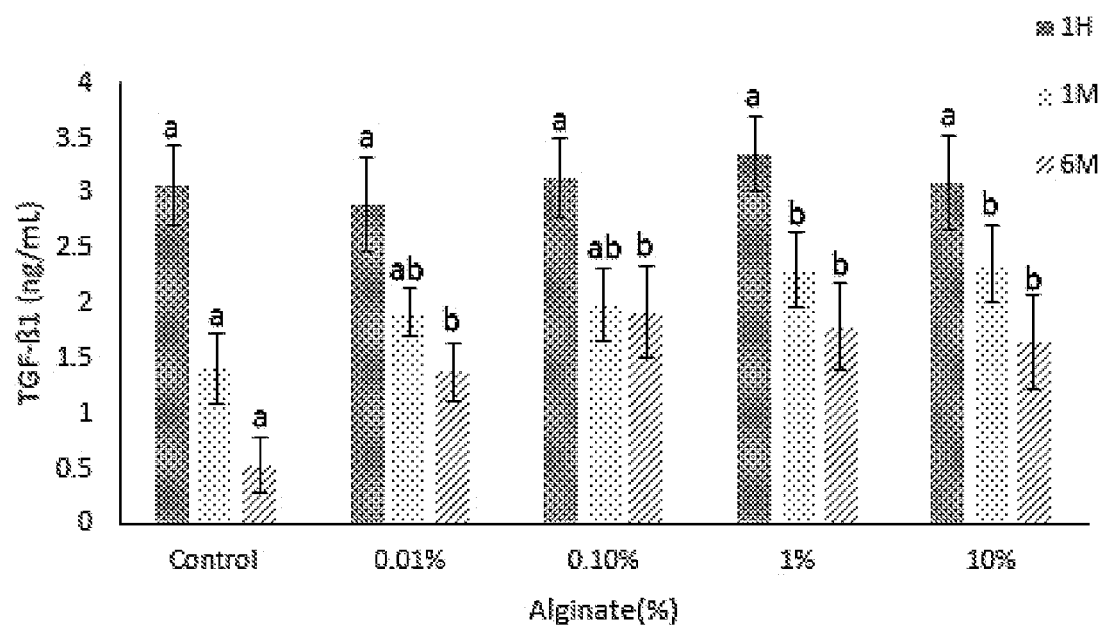
Figure 2C:
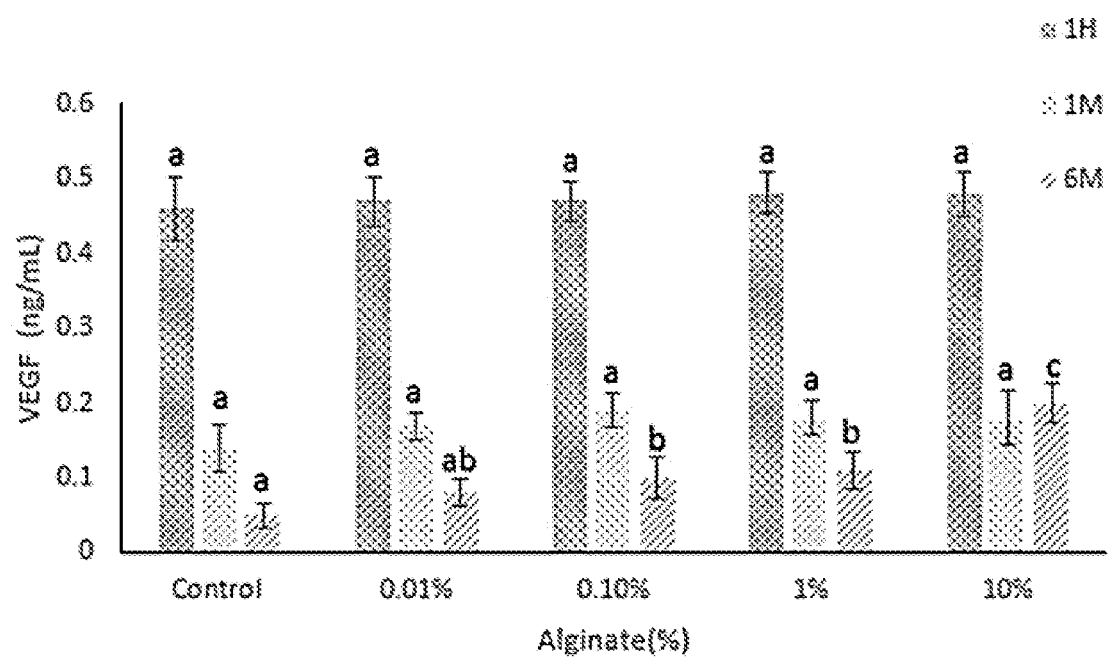
Figure 3A:
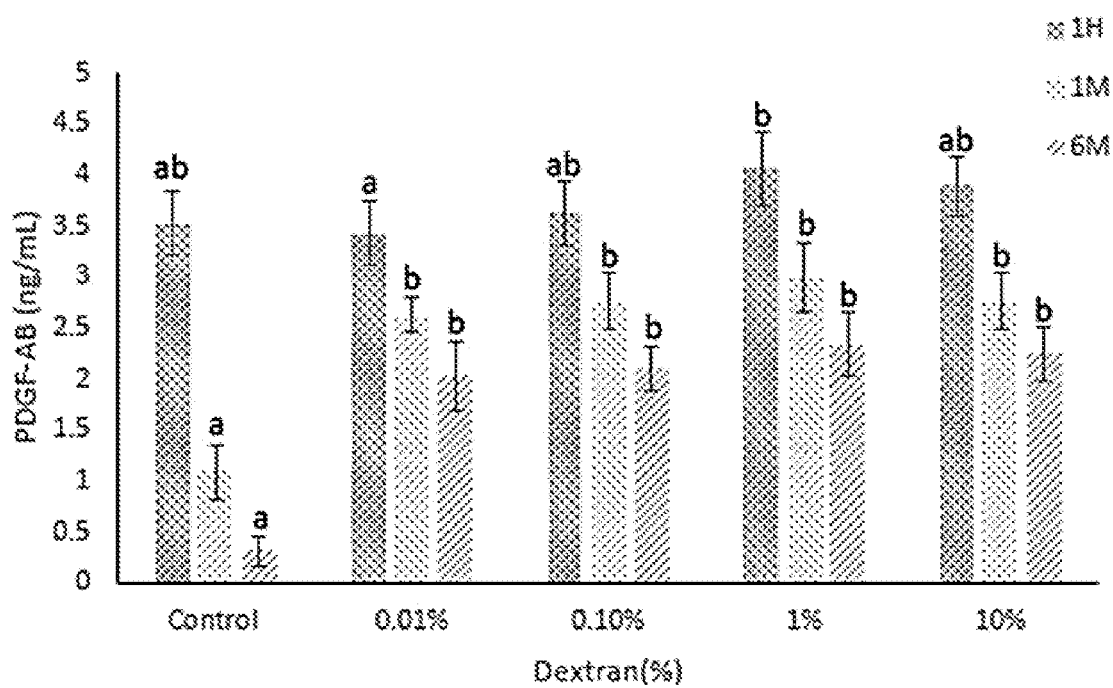
FIGS. 3A-3C show the growth factor levels in the plasma reconstituted from the plasma powder using dextran as a protectant.
Figure 3B:
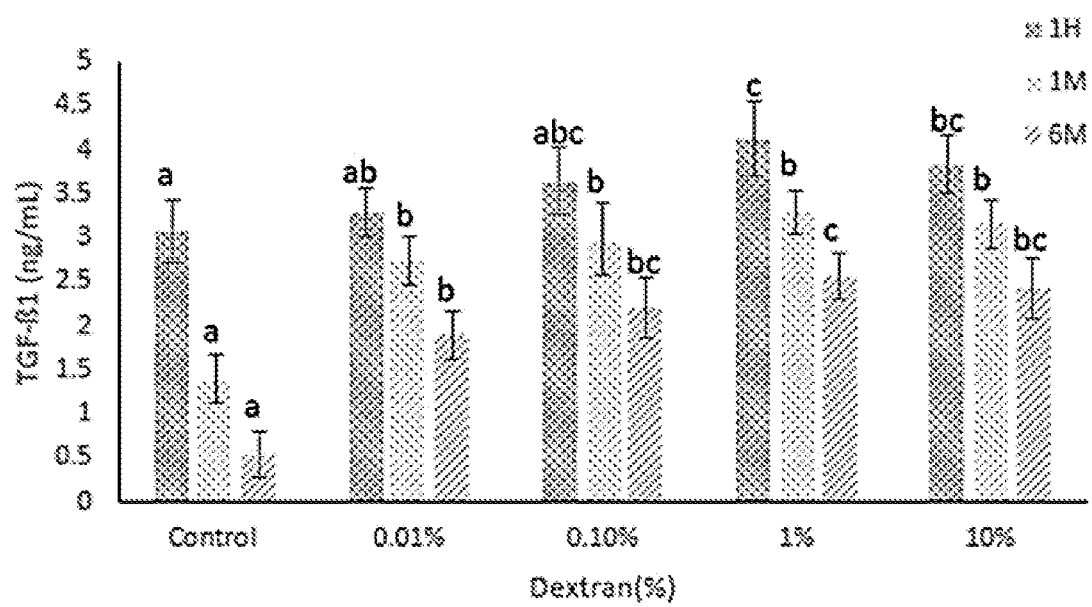
Figure 3C:
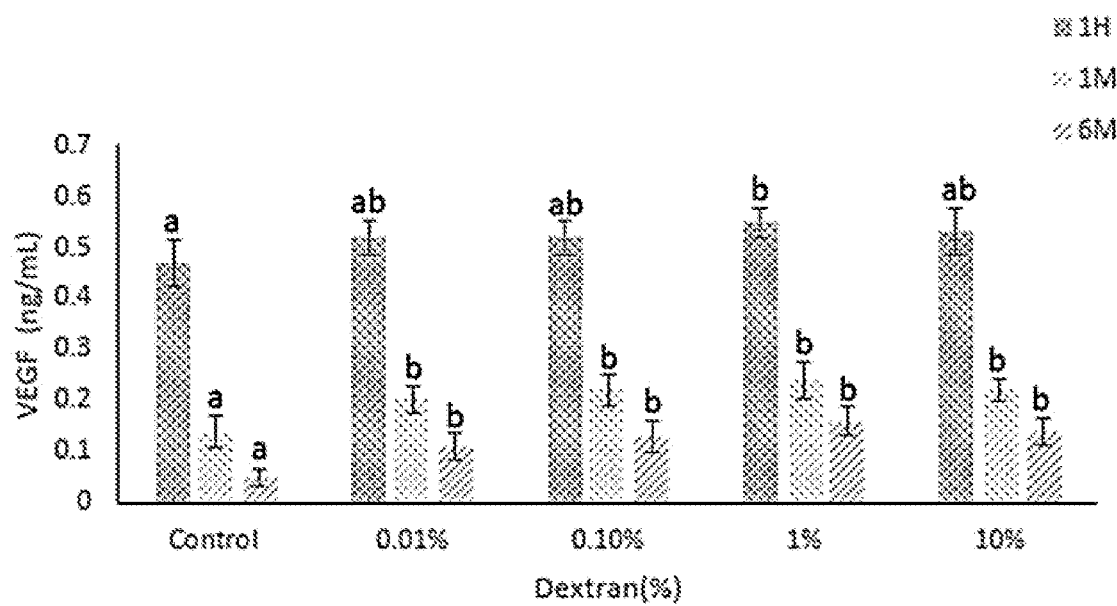
Figure 4A:
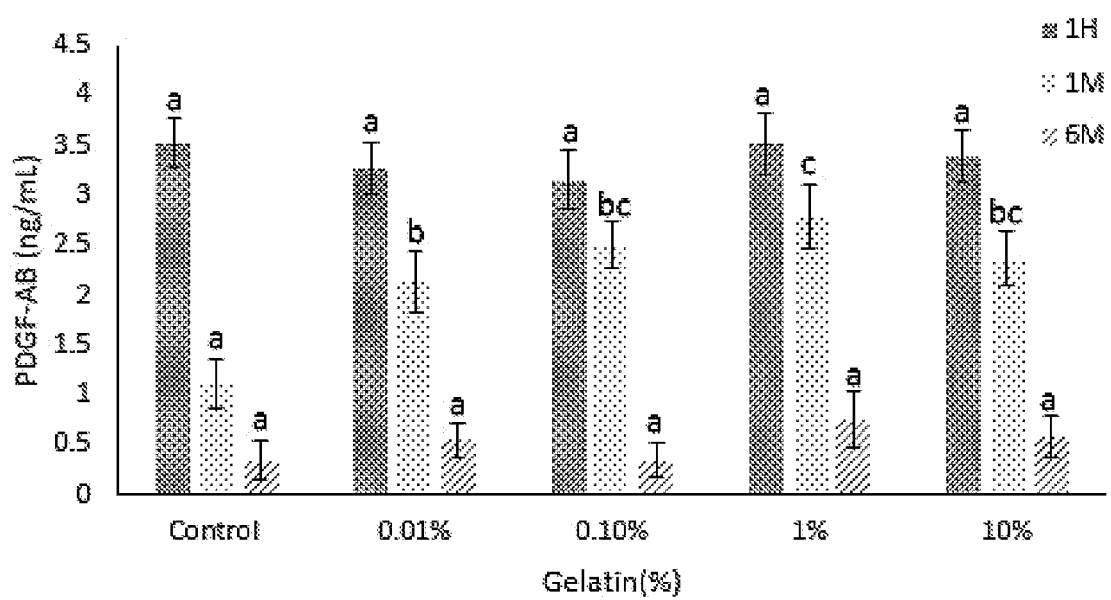
FIGS. 4A-4C show the growth factor levels in the plasma reconstituted from the plasma powder using gelatin as a protectant.
Figure 4B:
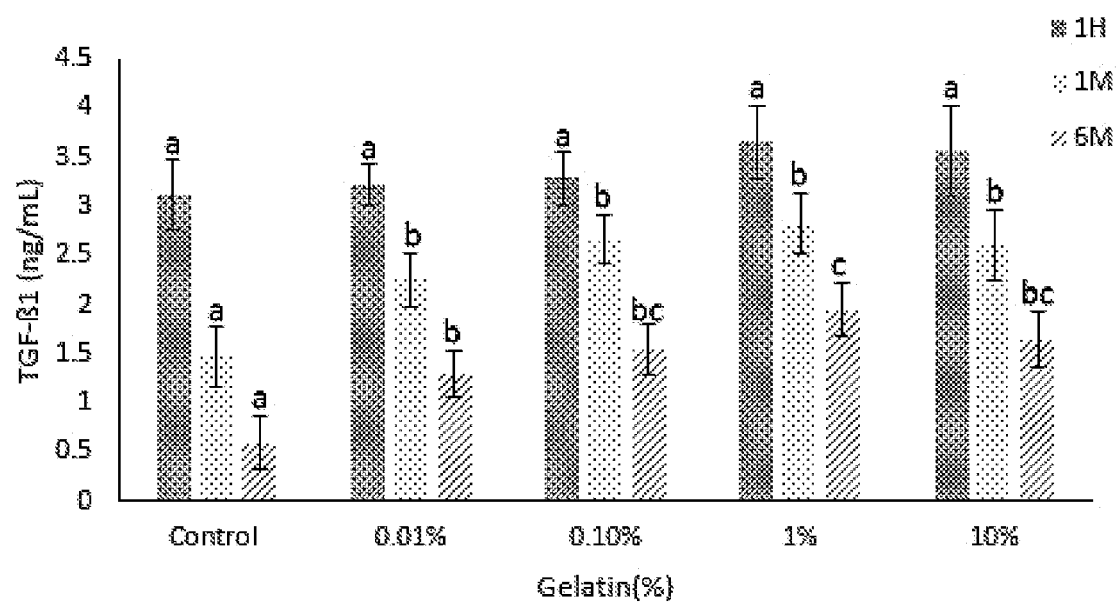
Figure 4C:
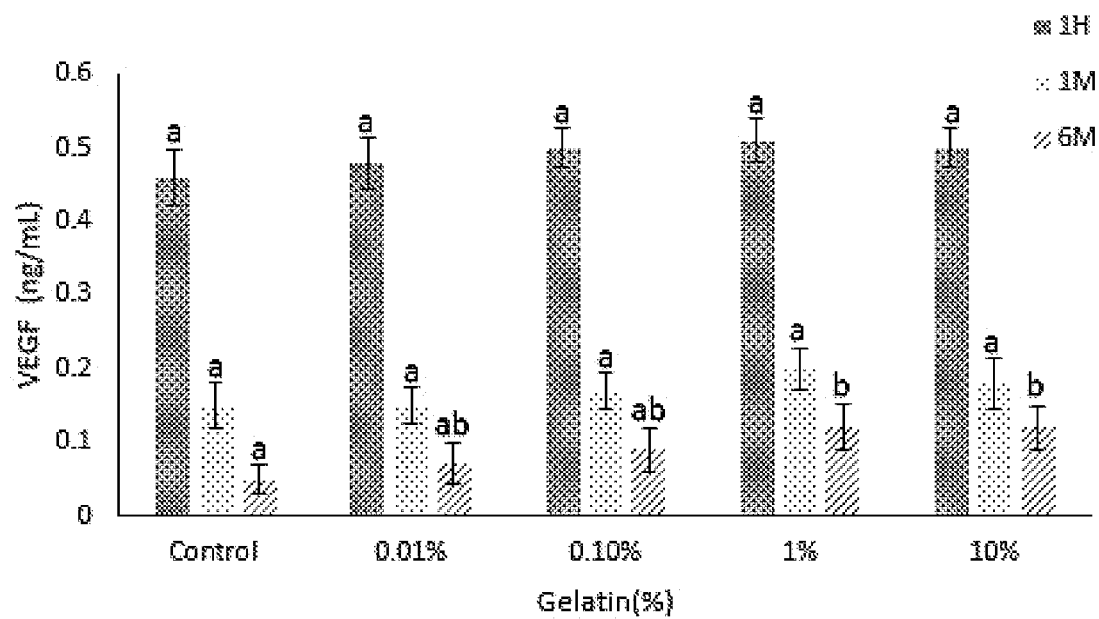
Figure 5A:
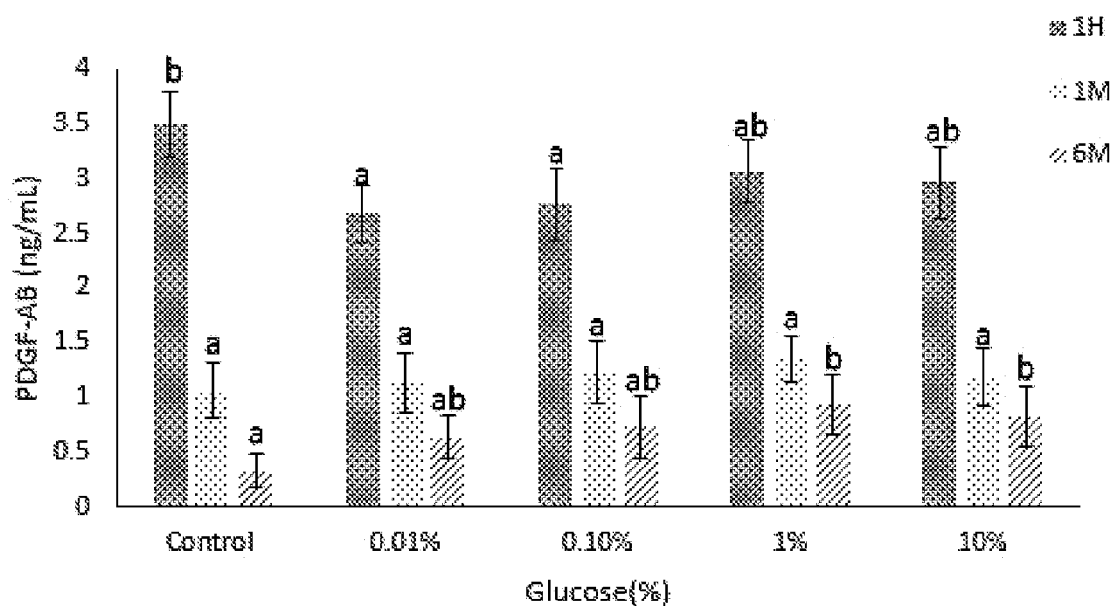
FIGS. 5A-5C show the growth factor levels in the plasma reconstituted from the plasma powder using glucose as a protectant.
Figure 5B:
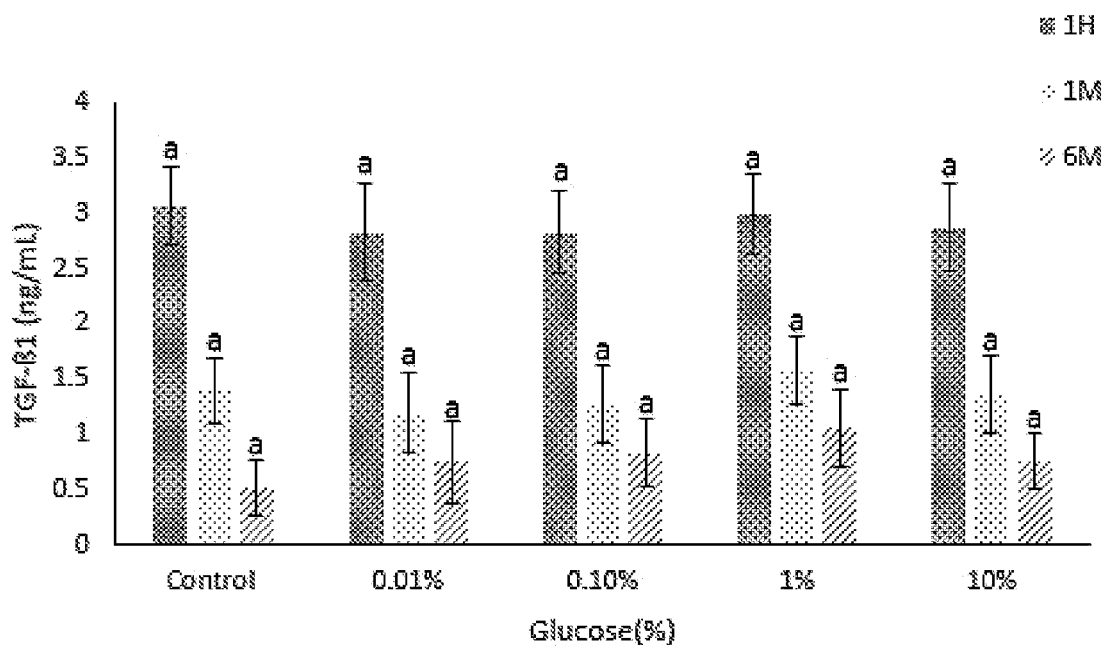
Figure 5C:
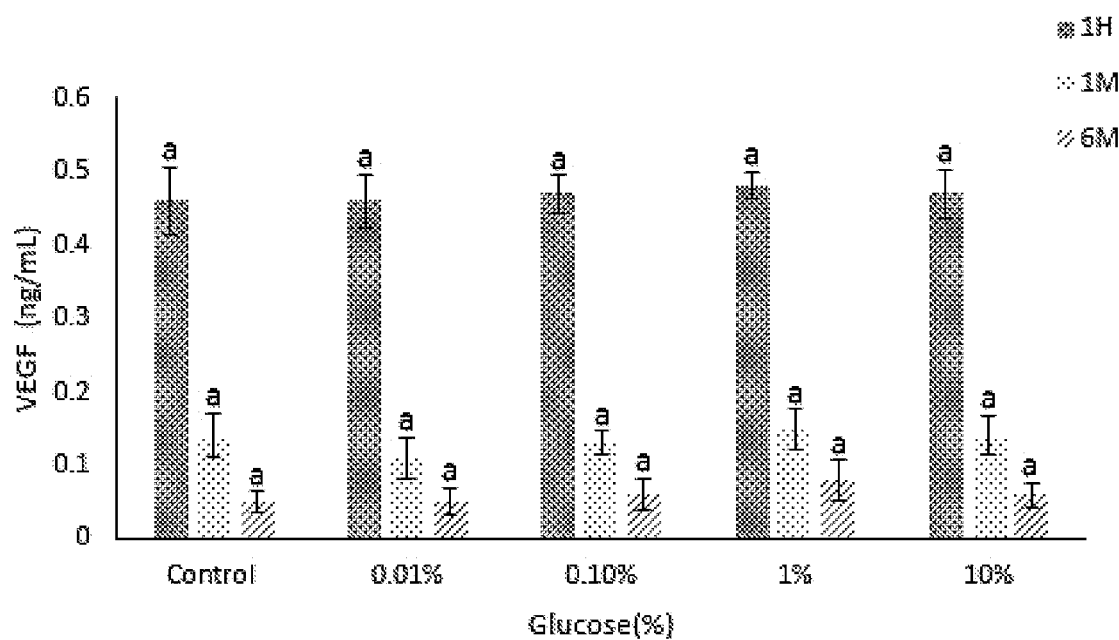
Figure 6A:
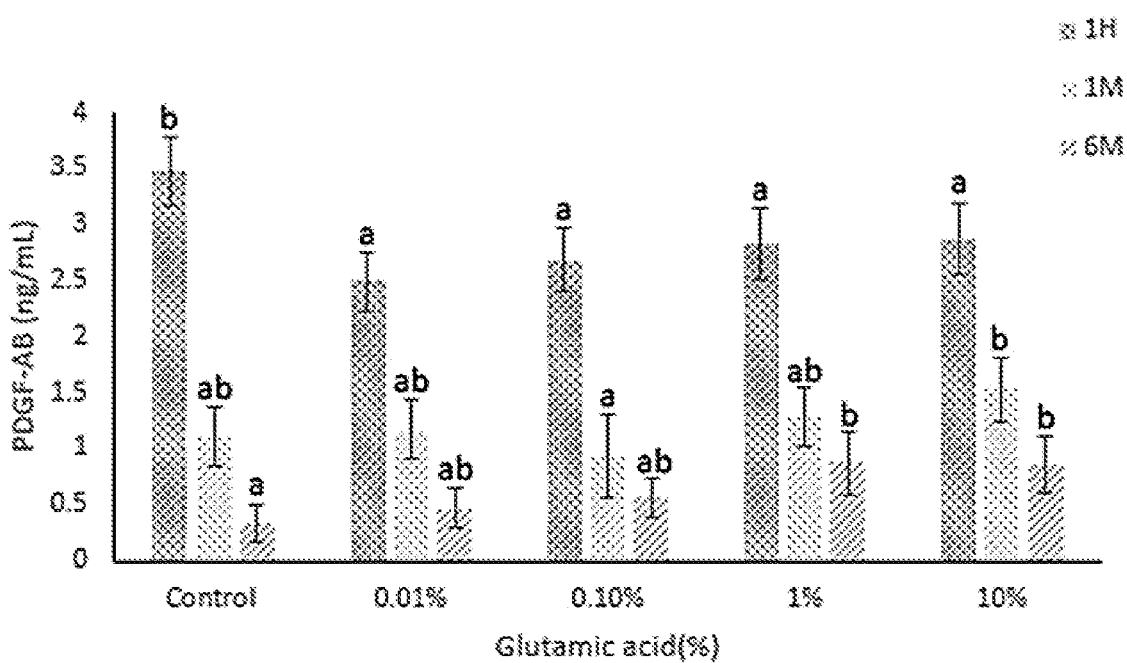
FIGS. 6A-6C show the growth factor levels in the plasma reconstituted from the plasma powder using glutamic acid as a protectant.
Figure 6B:
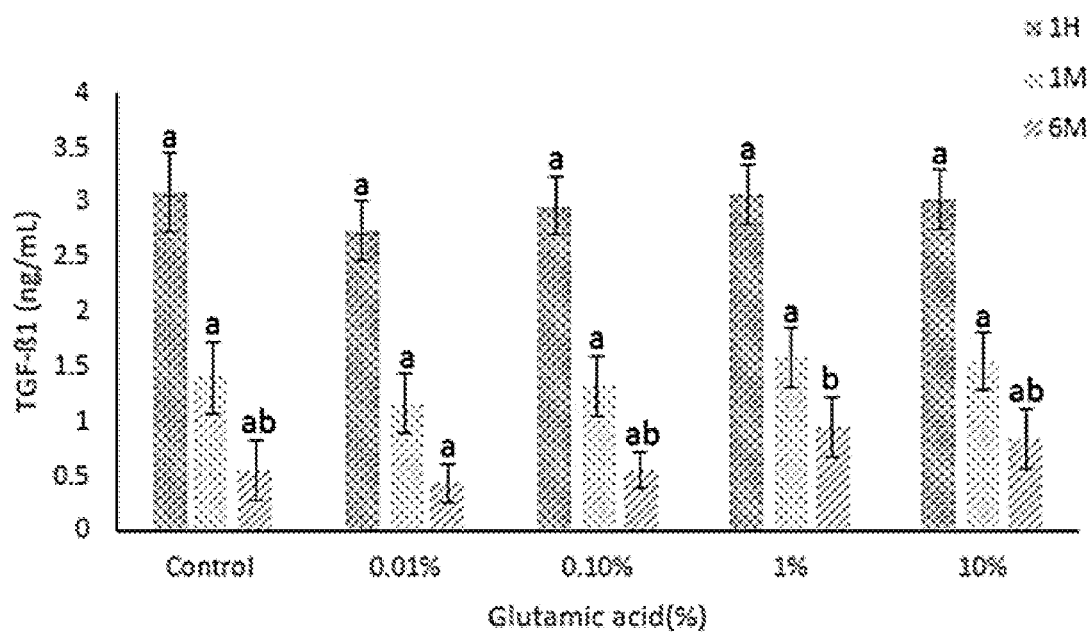
Figure 6C:
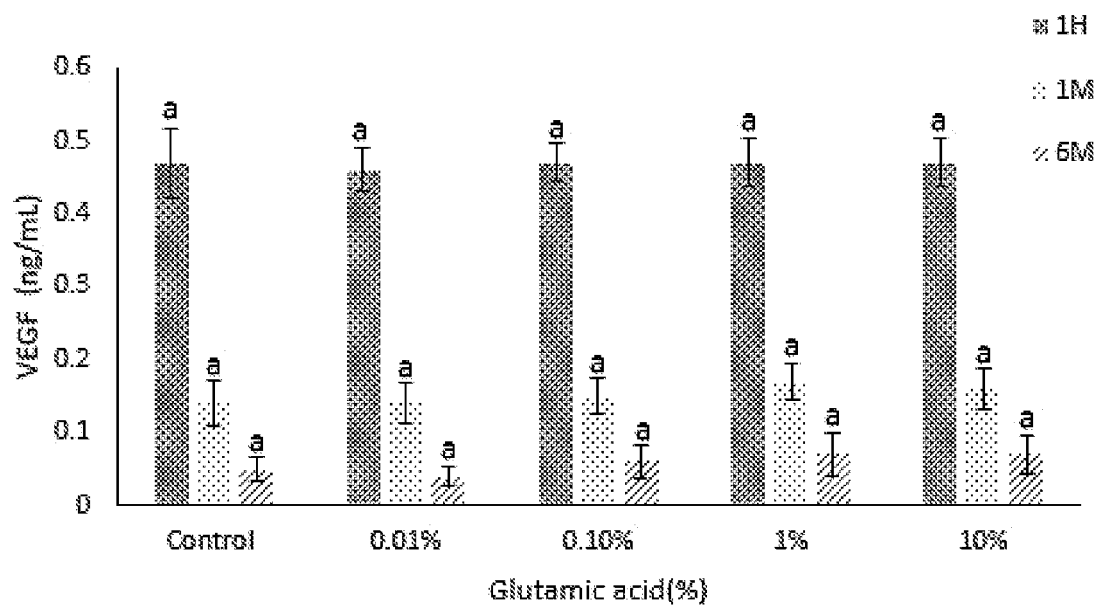
Figure 7A:
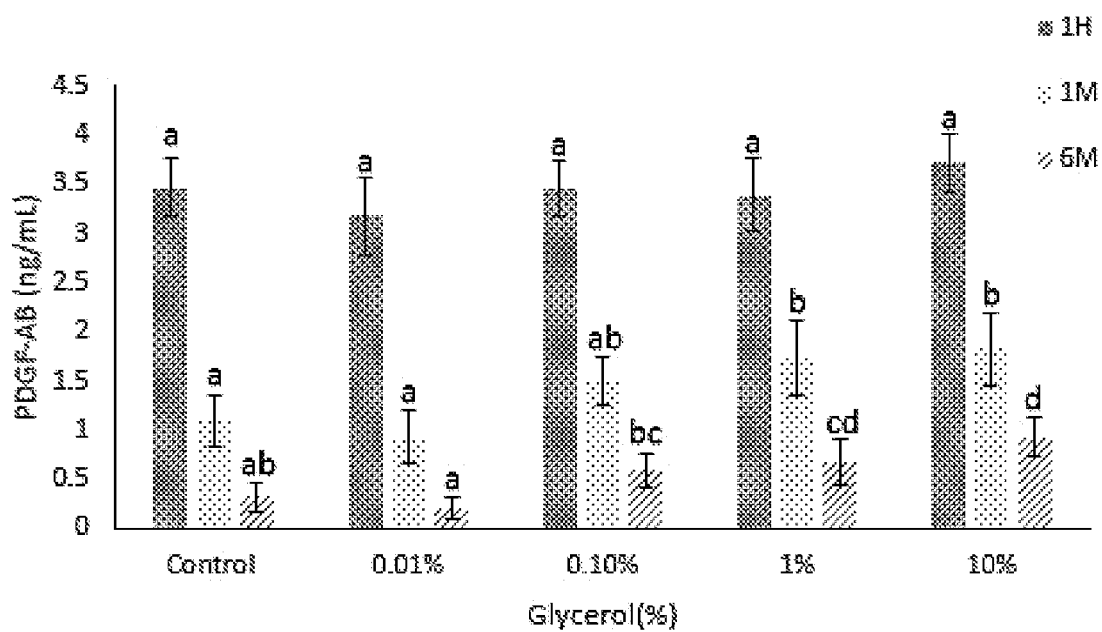
FIGS. 7A-7C show the growth factor levels in the plasma reconstituted from the plasma powder using glycerol as a protectant.
Figure 7B:
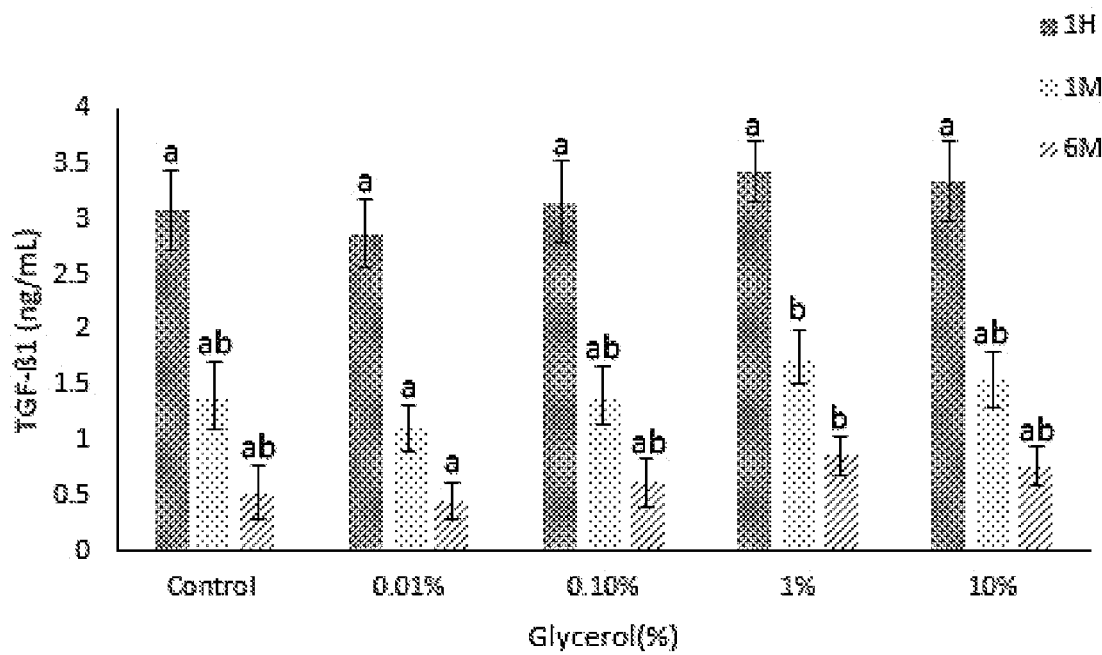
Figure 7C:
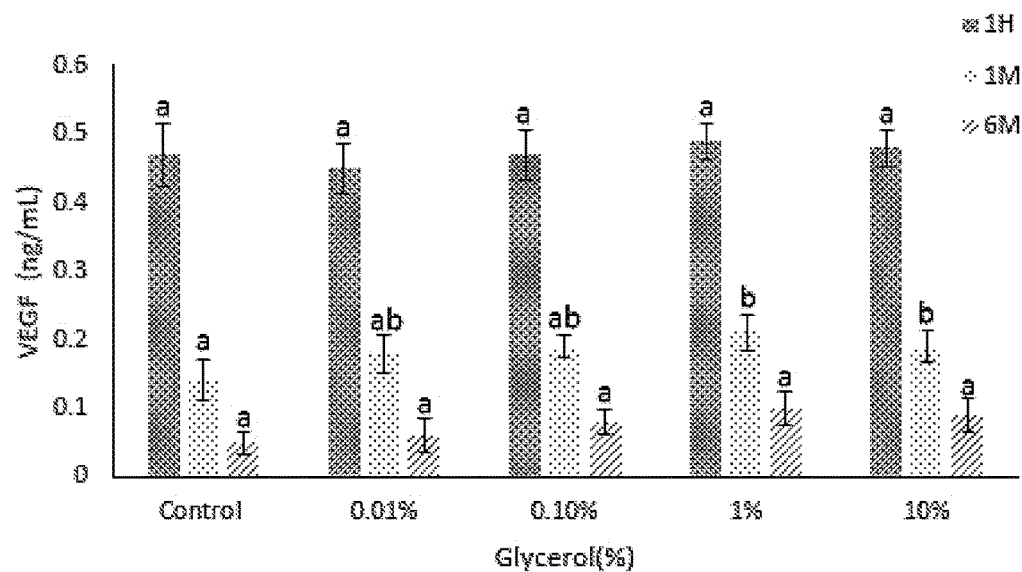
Figure 8A:
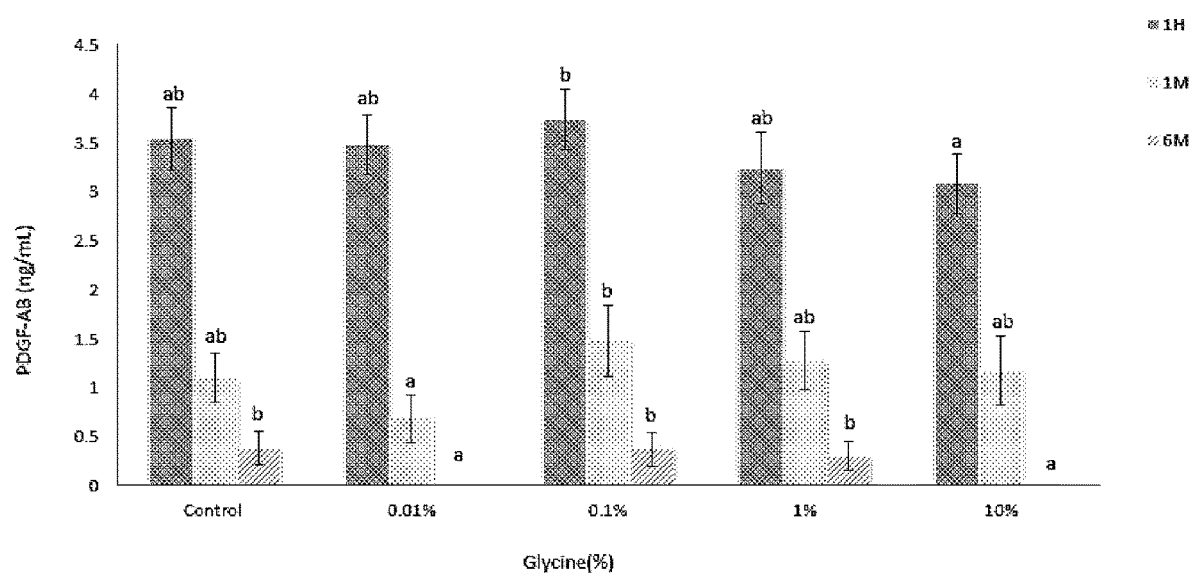
FIGS. 8A-8C show the growth factor levels in the plasma reconstituted from the plasma powder using glycine as a protectant.
Figure 8B:
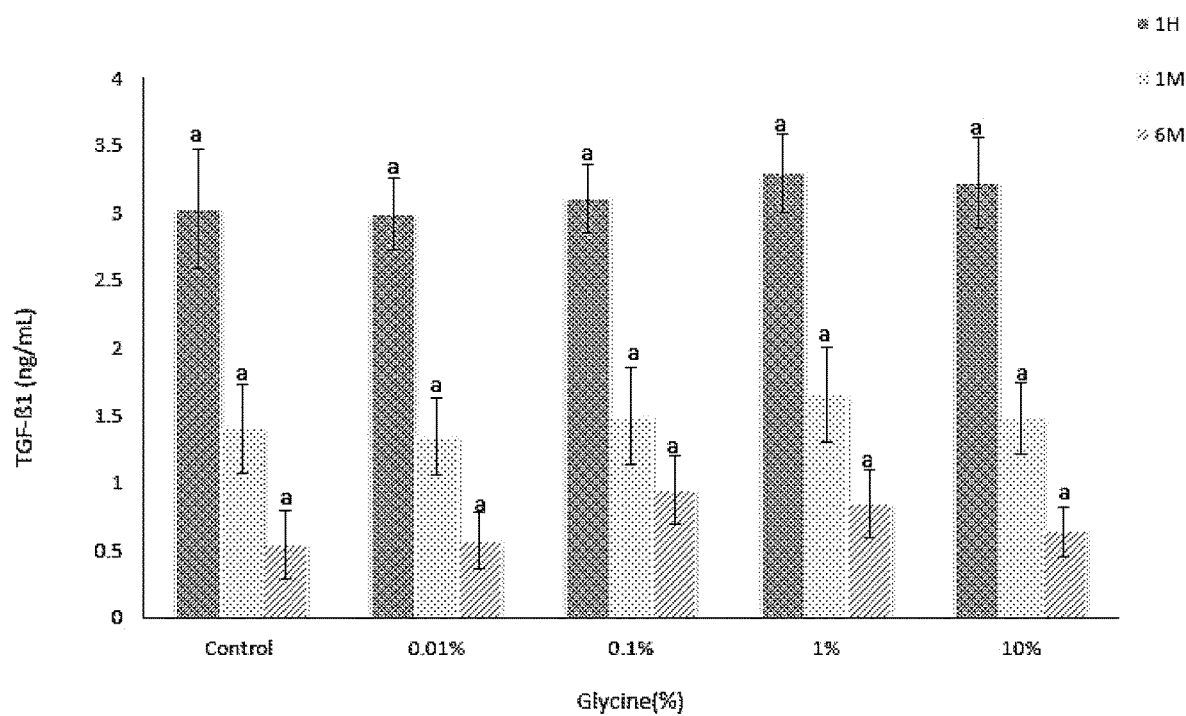
Figure 8C:
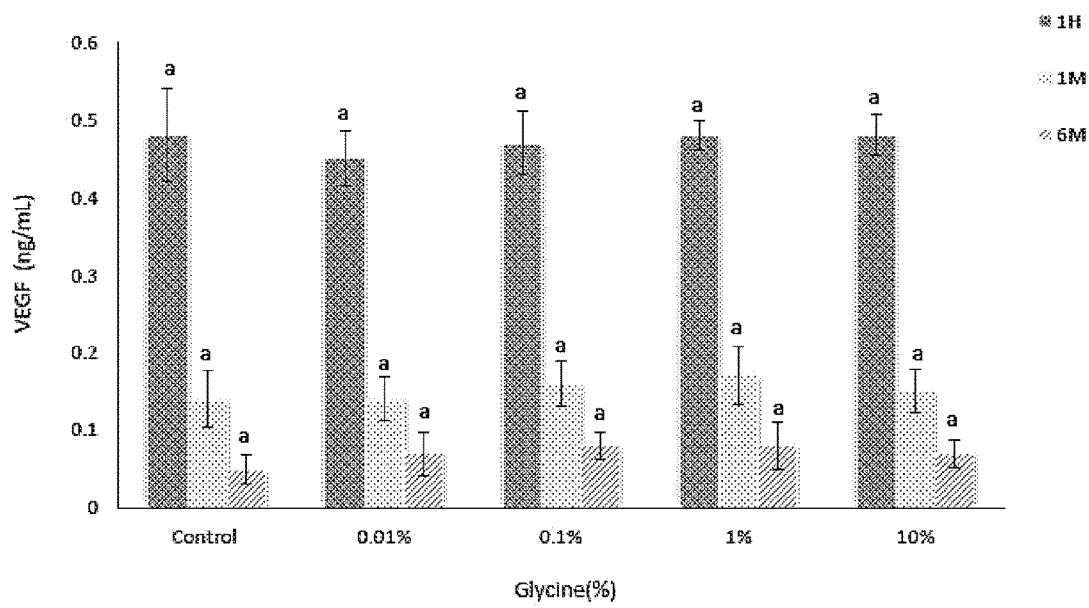
Figure 9A:
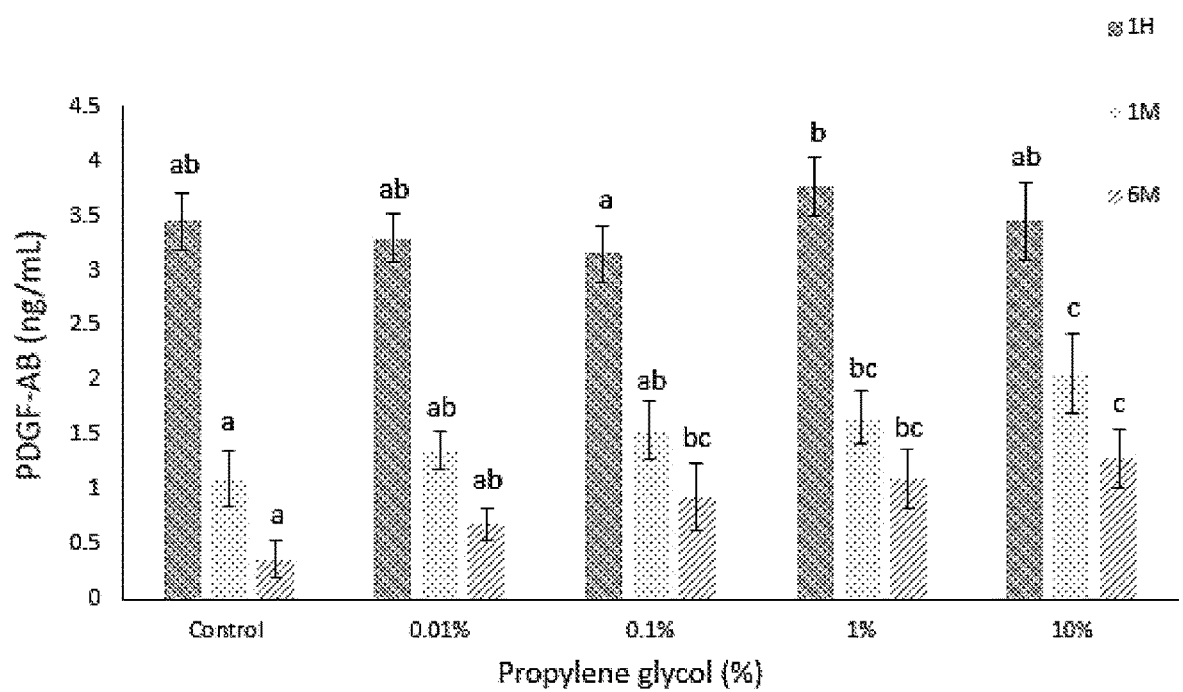
FIGS. 9A-9C show the growth factor levels in the plasma reconstituted from the plasma powder using propylene glycol as a protectant.
Figure 9B:
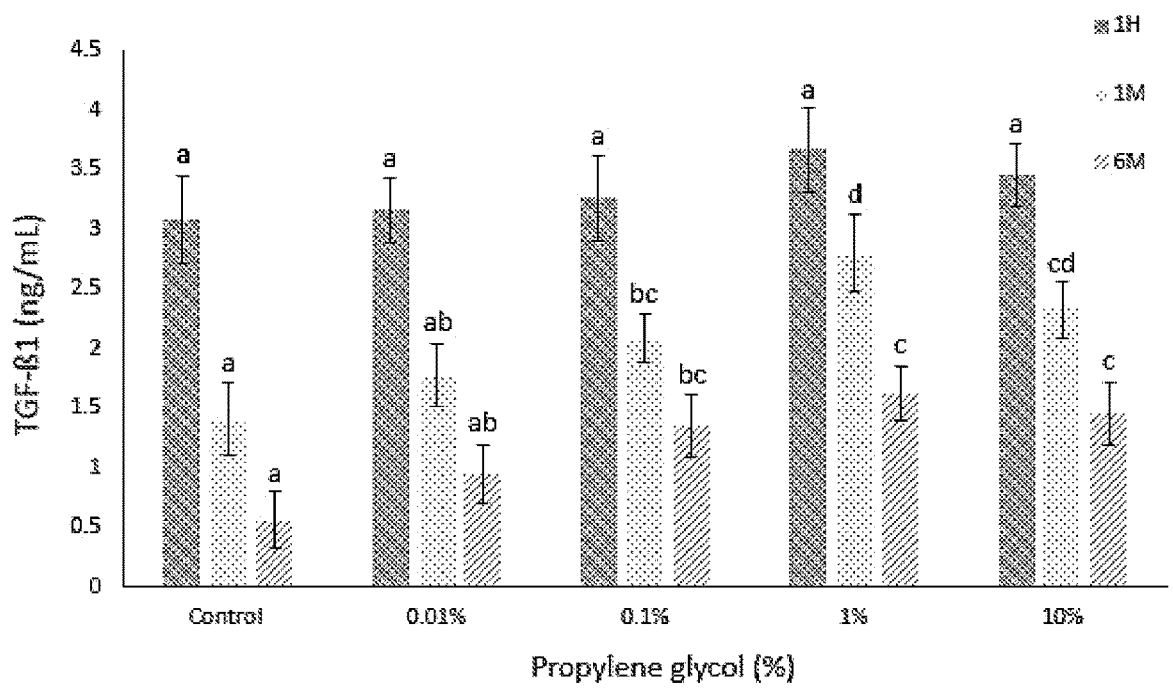
Figure 9C:
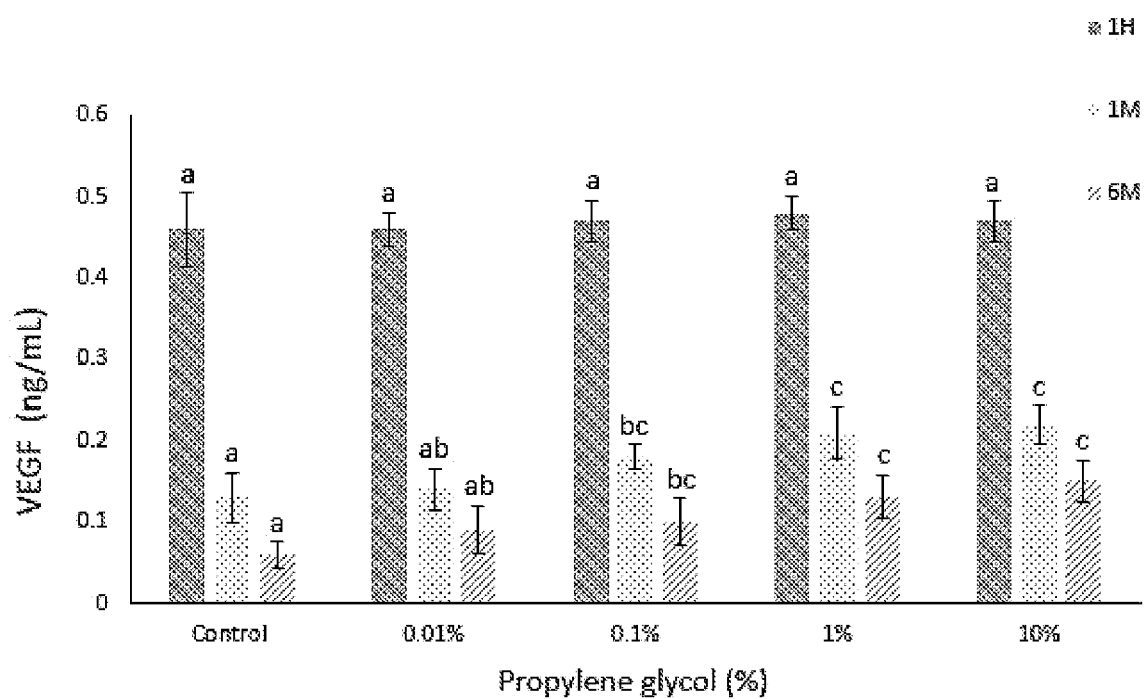
Figure 10A:
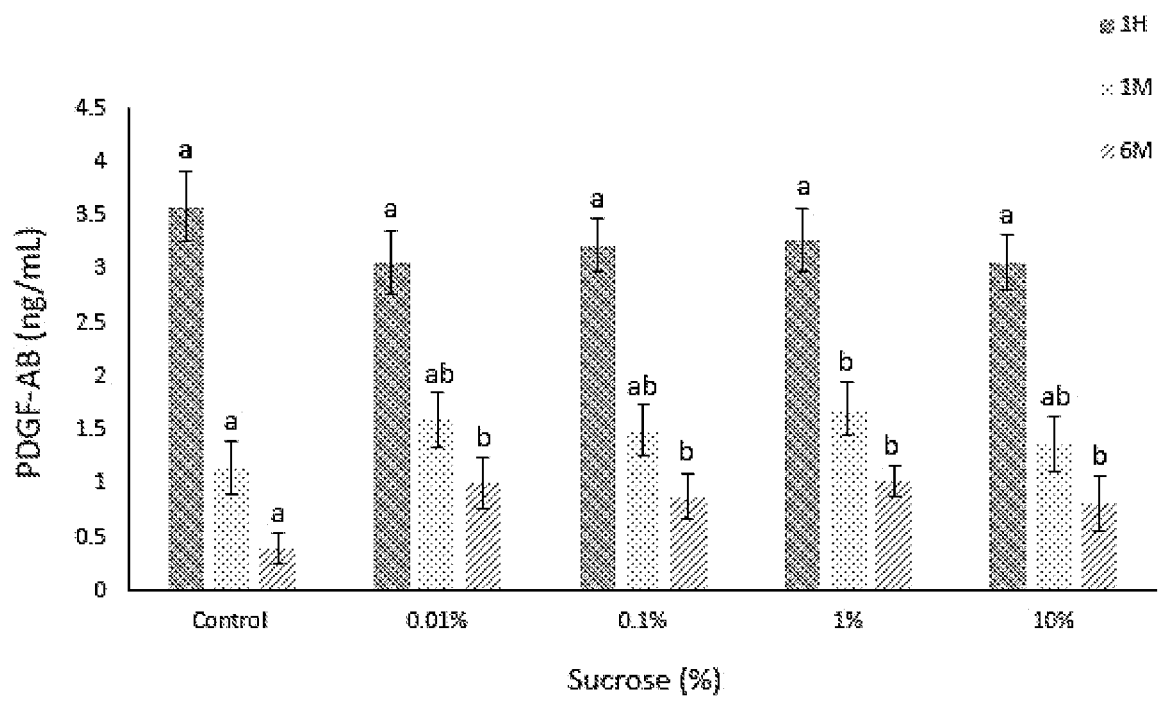
FIGS. 10A-10C show the growth factor levels in the plasma reconstituted from the plasma powder using sucrose as a protectant.
Figure 10B:
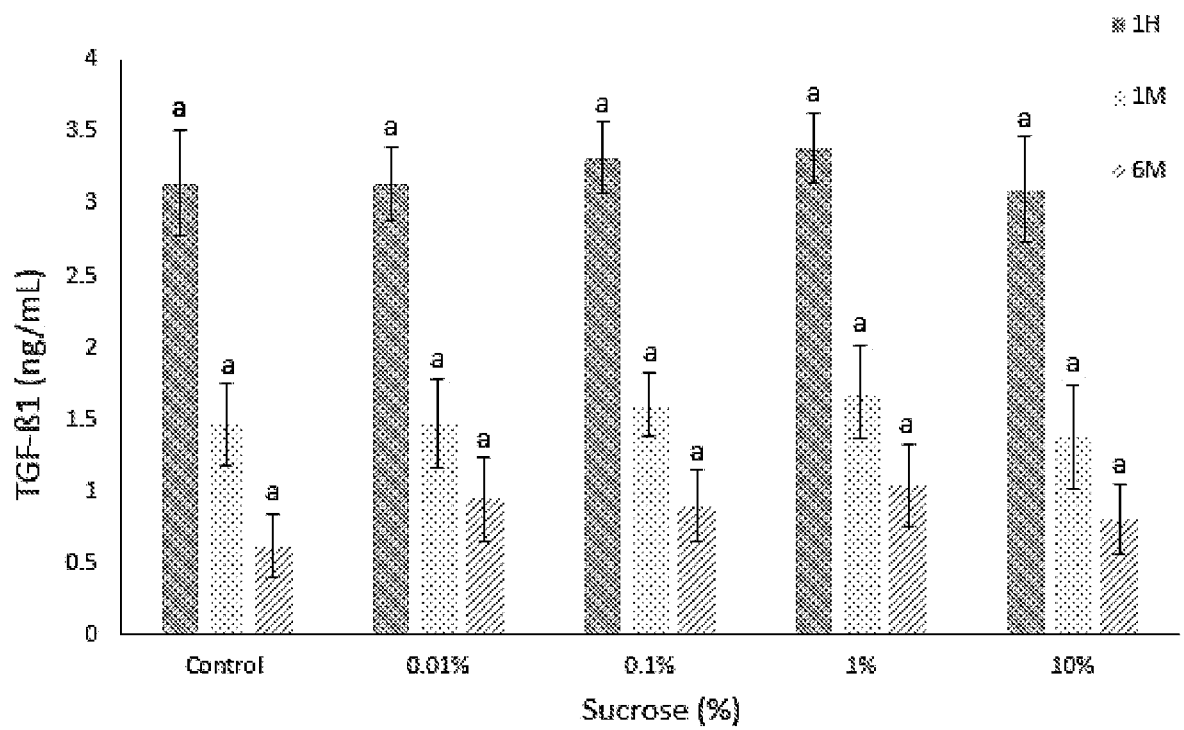
Figure 10C:
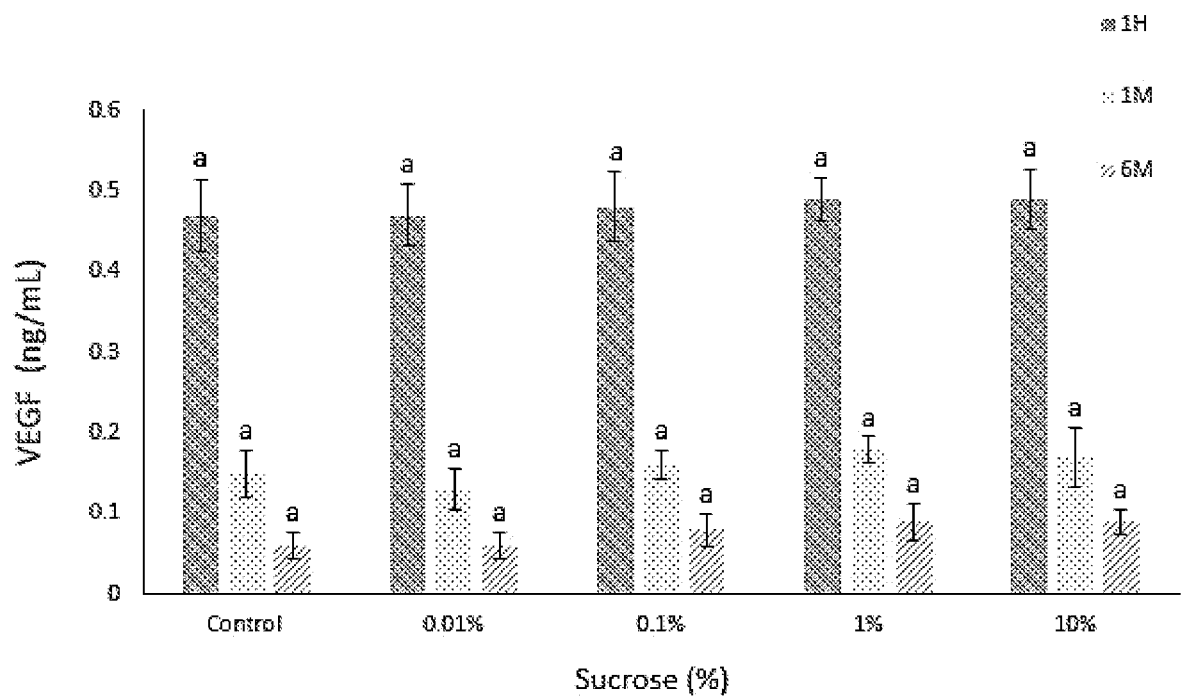
Figure 11A:
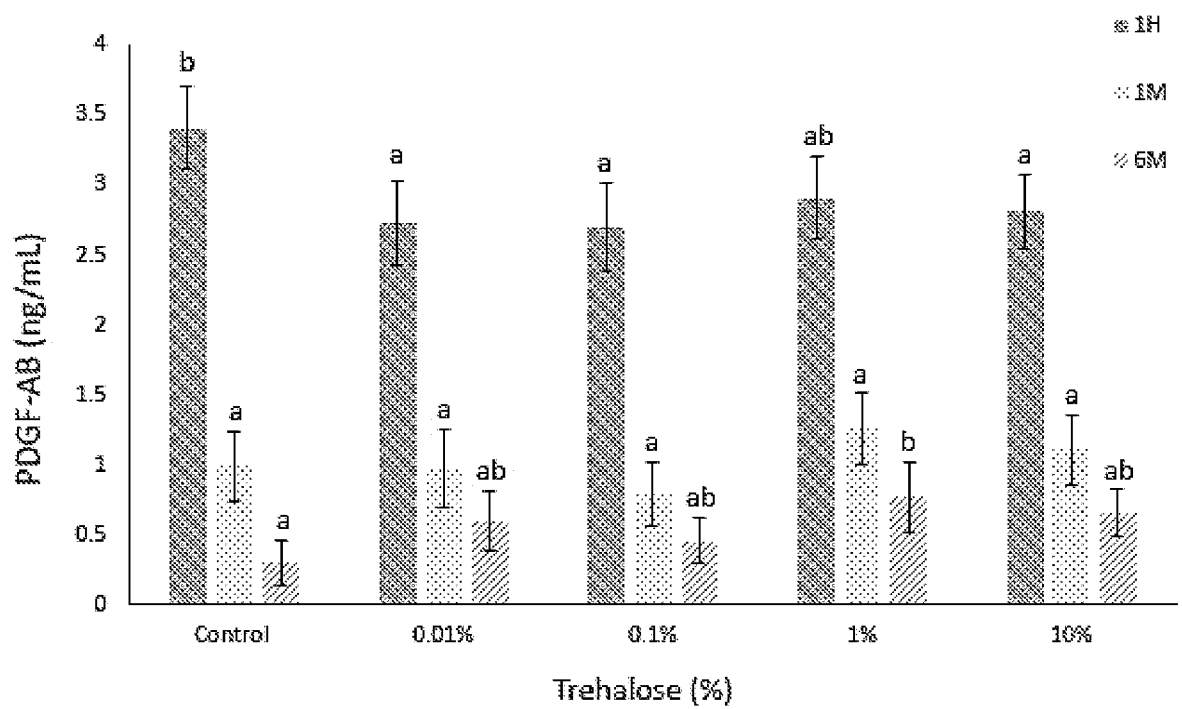
FIGS. 11A-11C show the growth factor levels in the plasma reconstituted from the plasma powder using trehalose as a protectant.
Figure 11B:
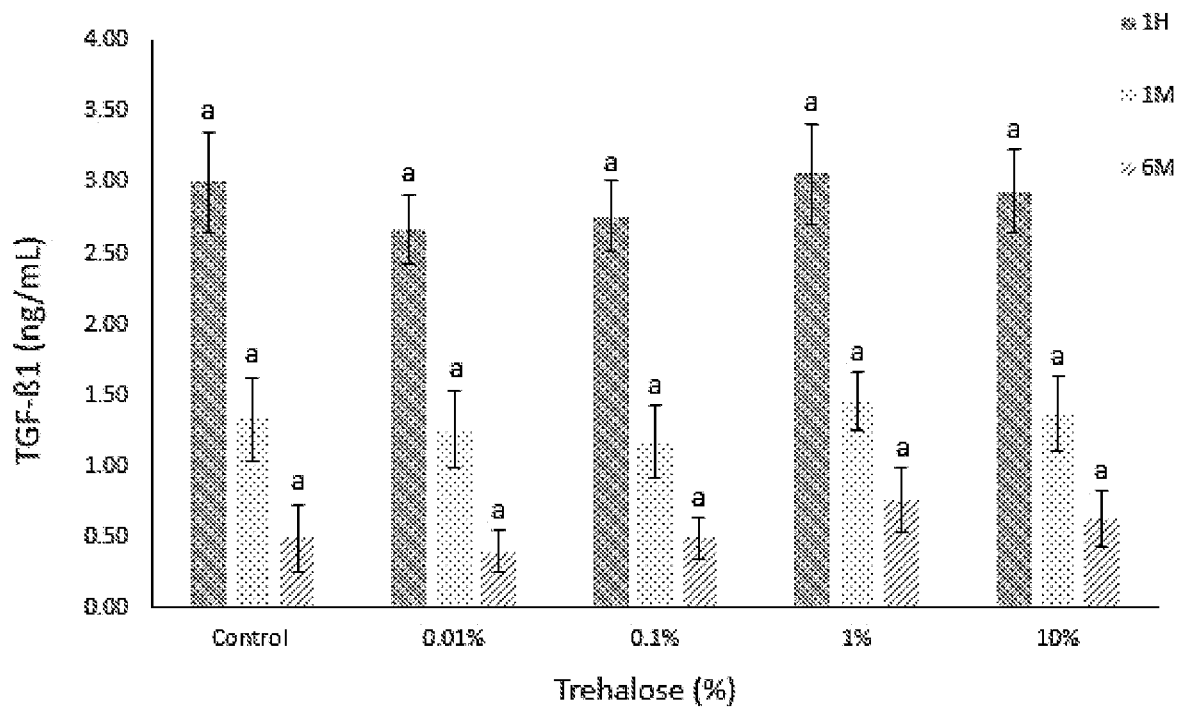
Figure 11C:
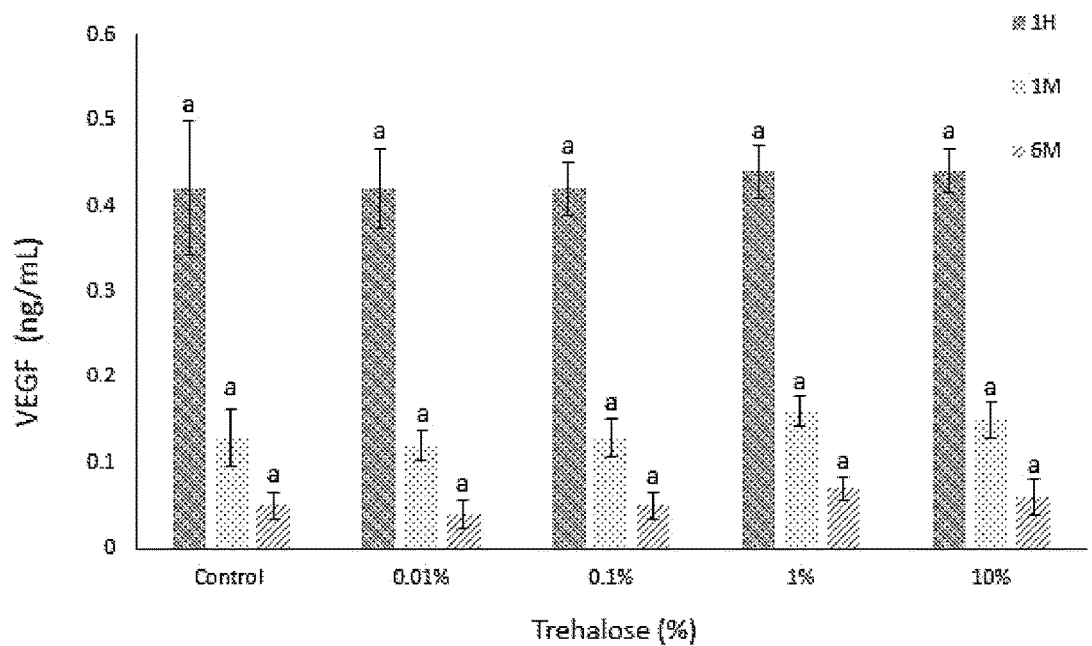
Figure 12A:
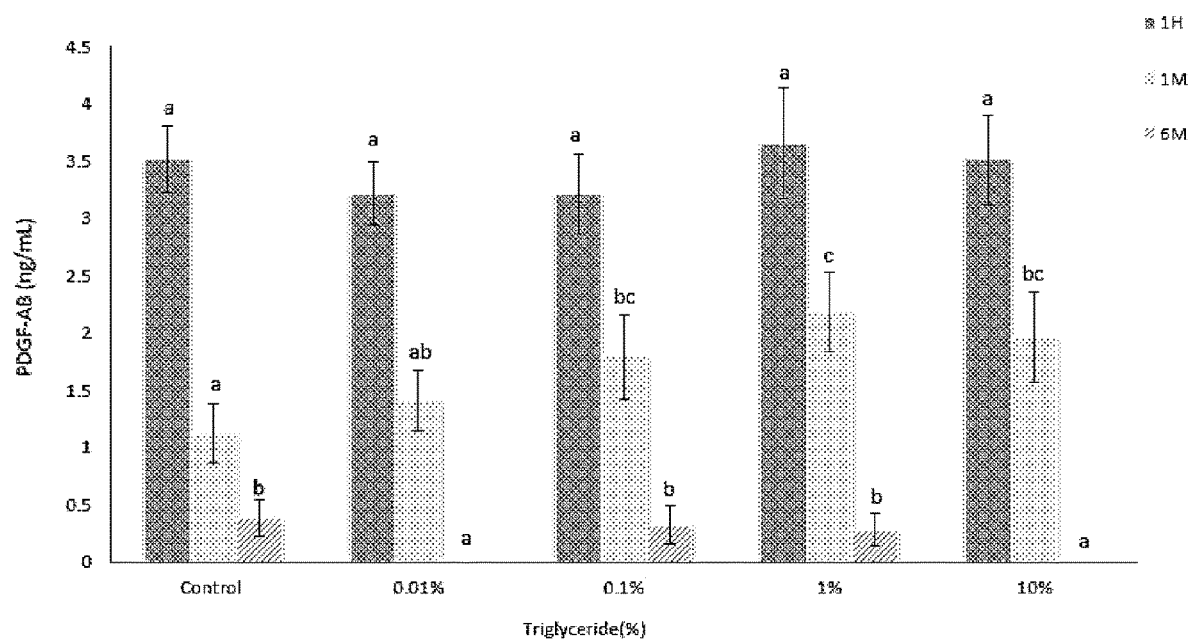
FIGS. 12A-12C show the growth factor levels in the plasma reconstituted from the plasma powder using triglyceride as a protectant.
Figure 12B:
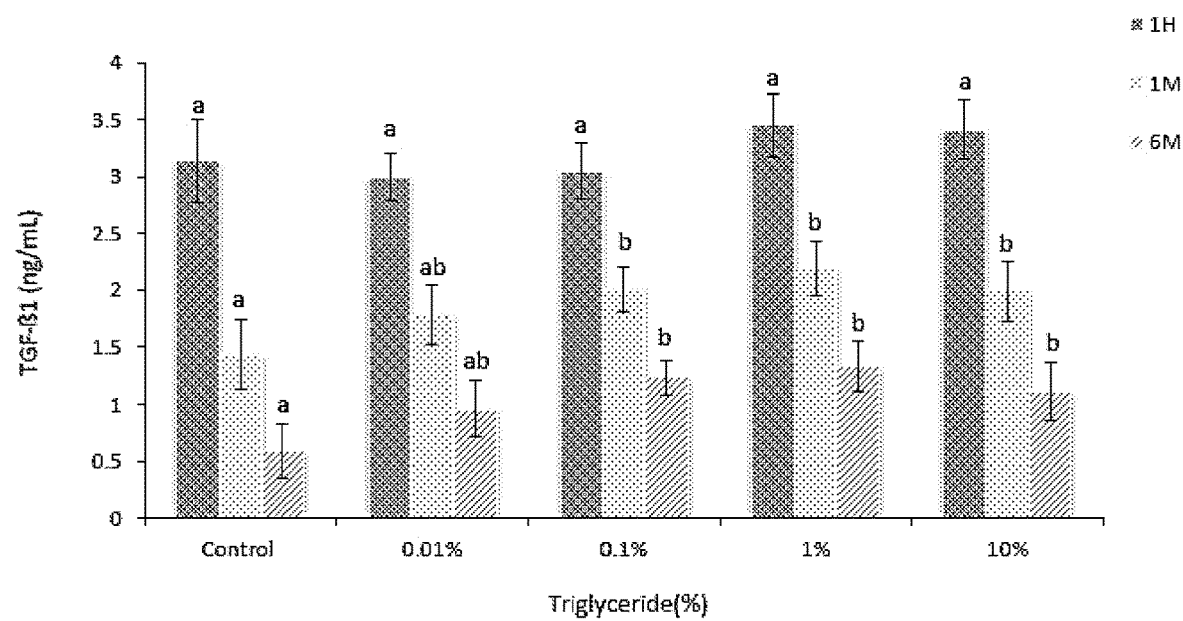
Figure 12C:
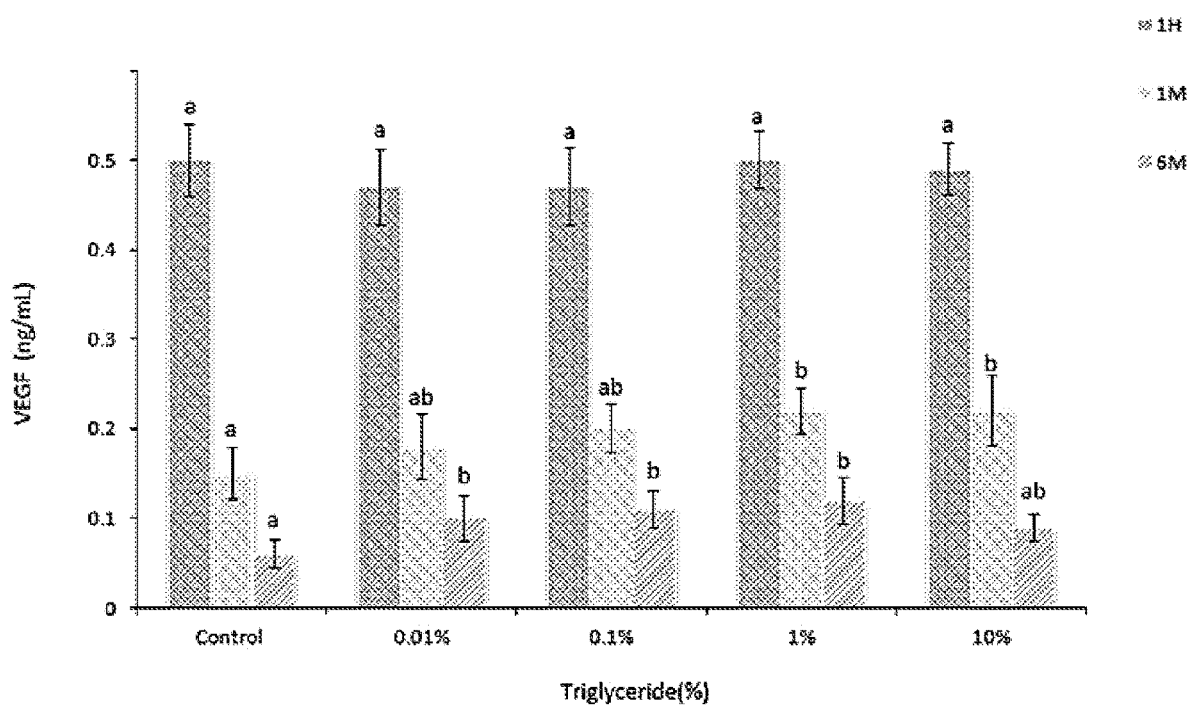
Figure 13A:
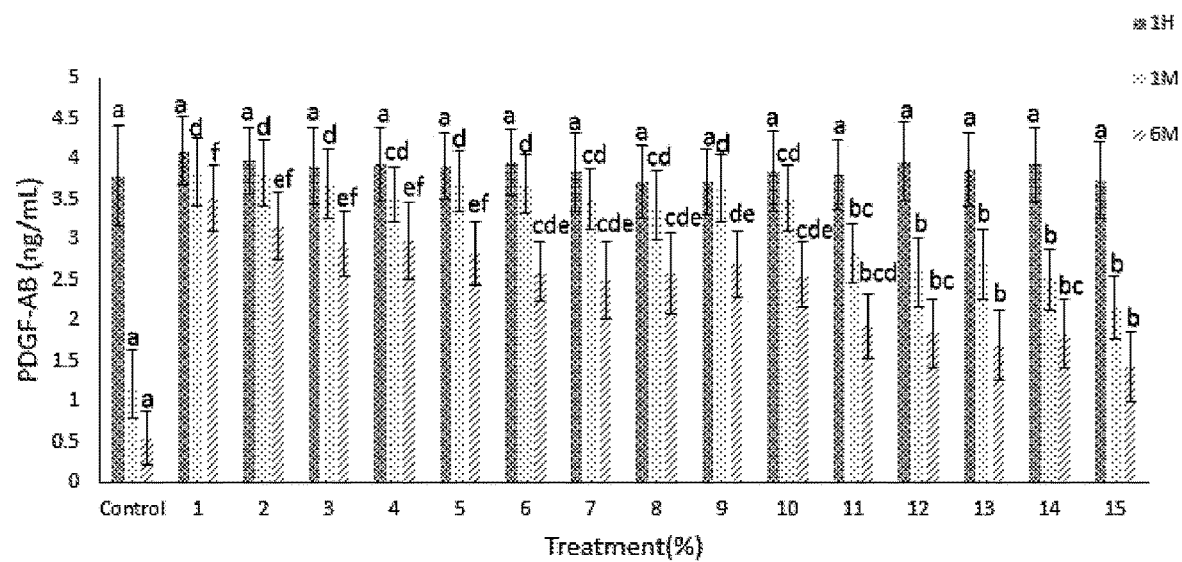
FIGS. 13A-13C show the growth factor levels in the plasma reconstituted from the plasma powder using two (2) protectants.
Figure 13B:
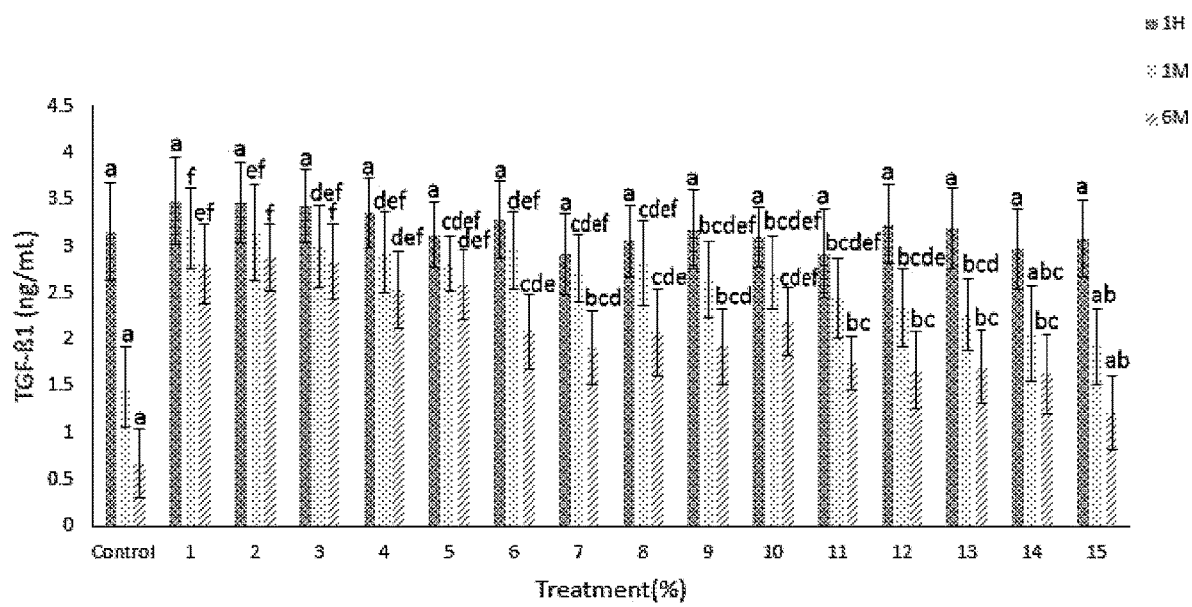
Figure 13C:
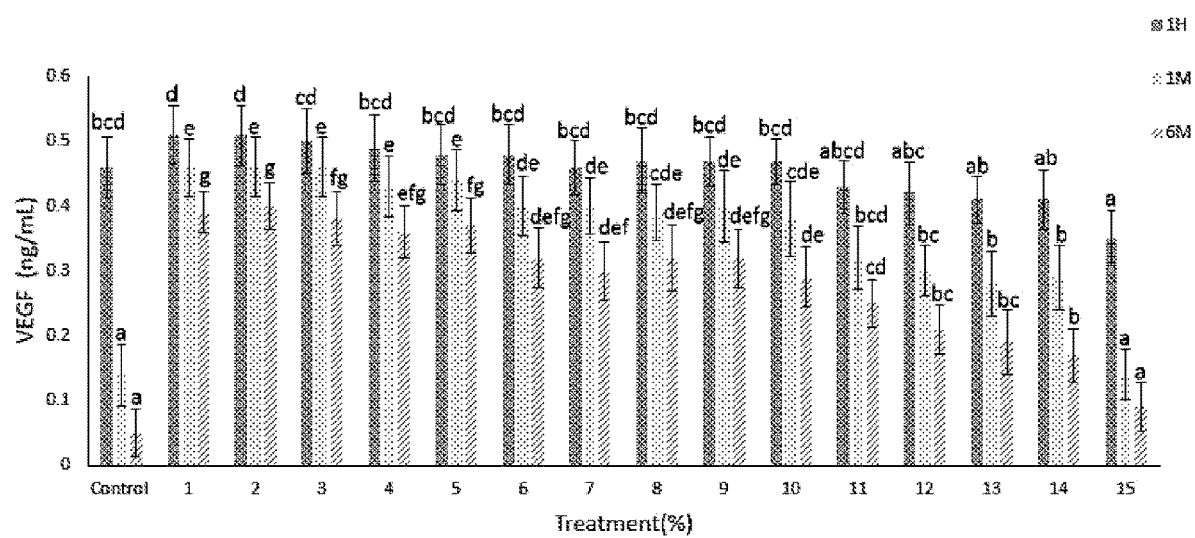
Figure 14A:
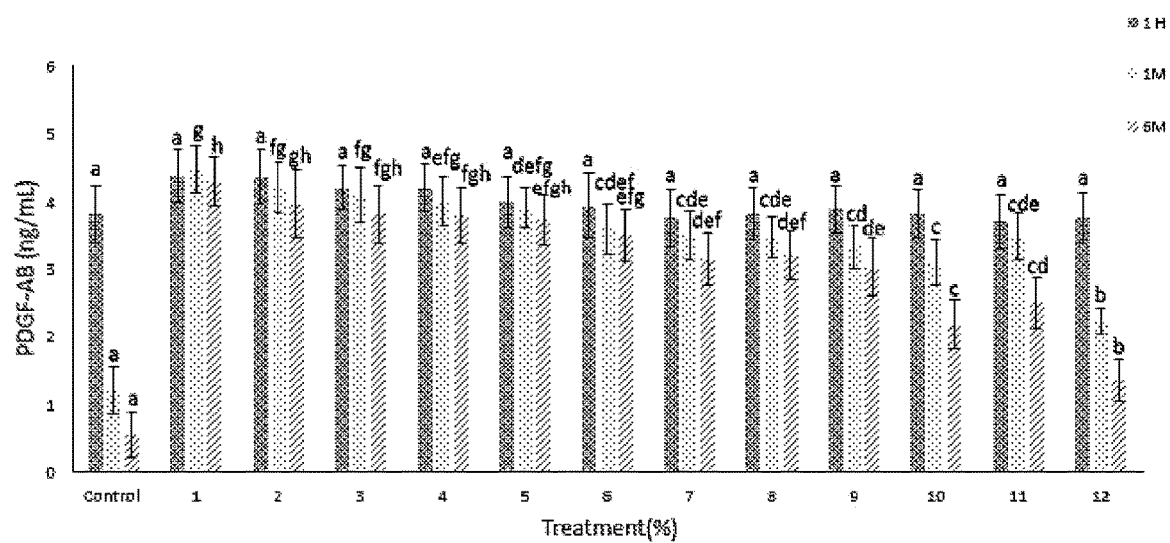
FIGS. 14A-14C show the growth factor levels in the plasma reconstituted from the plasma powder using three (3) protectants.
Figure 14B:
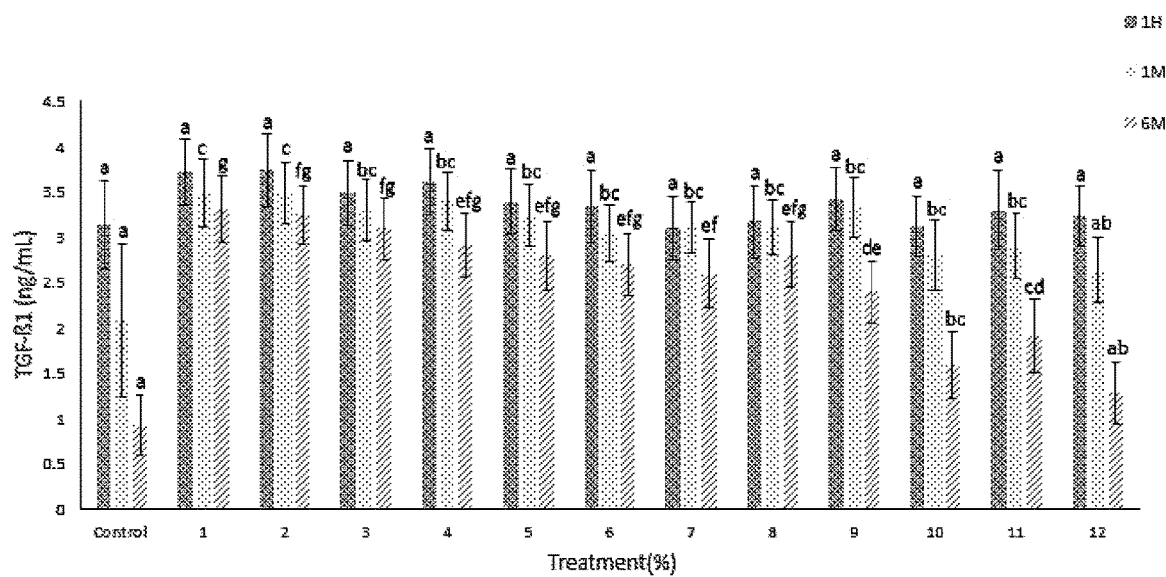
Figure 14C:
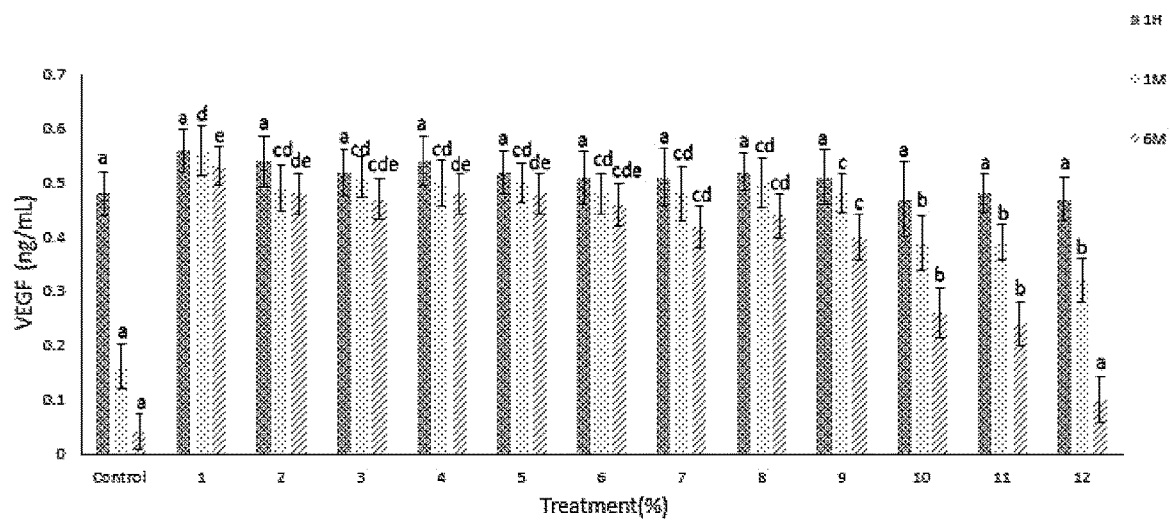
Figure 15A:
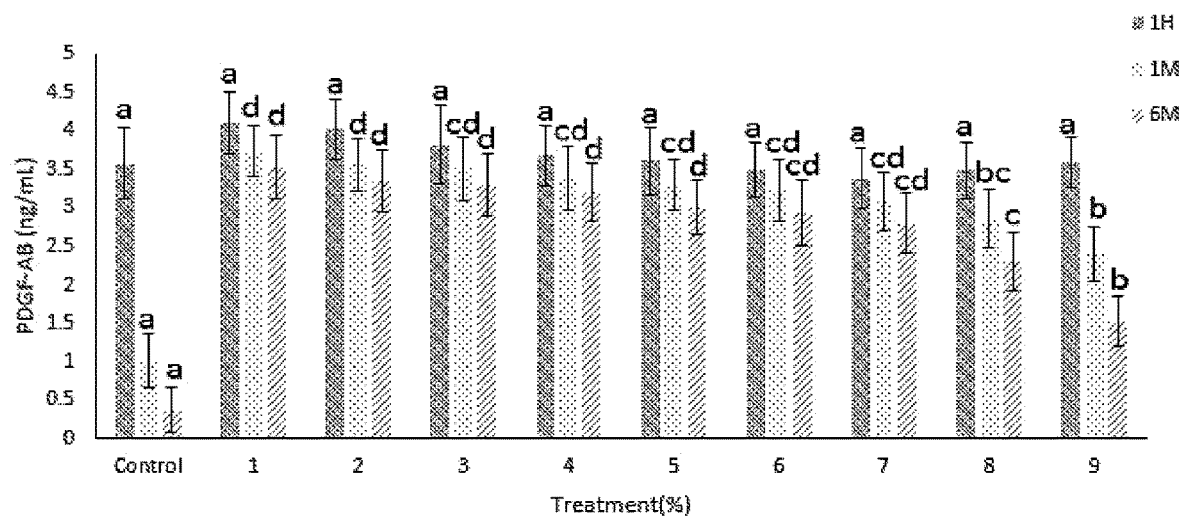
FIGS. 15A-15C show the growth factor levels in the plasma reconstituted from the plasma powder using four (4) protectants.
Figure 15B:
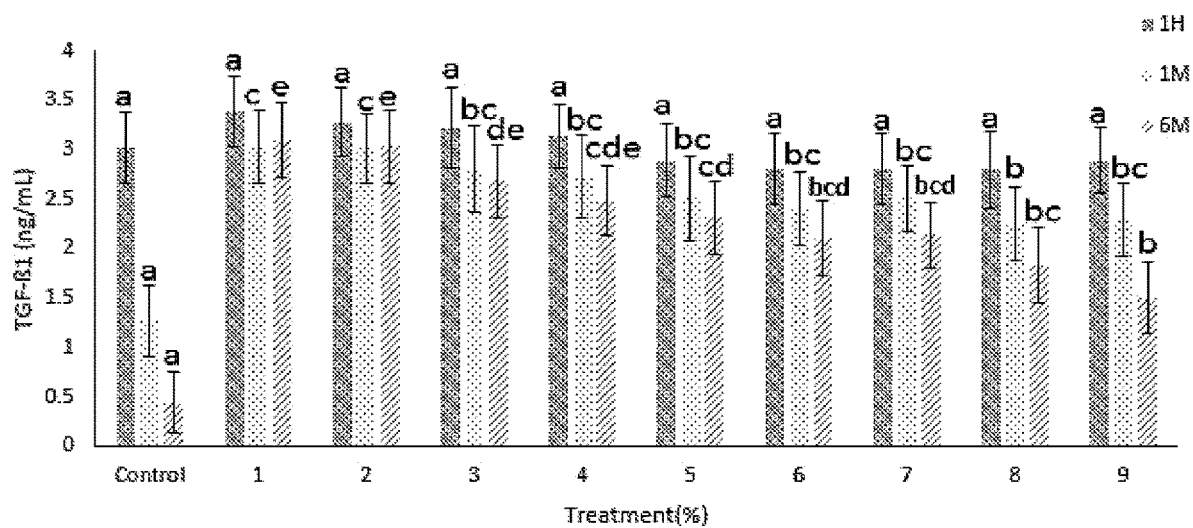
Figure 15C:
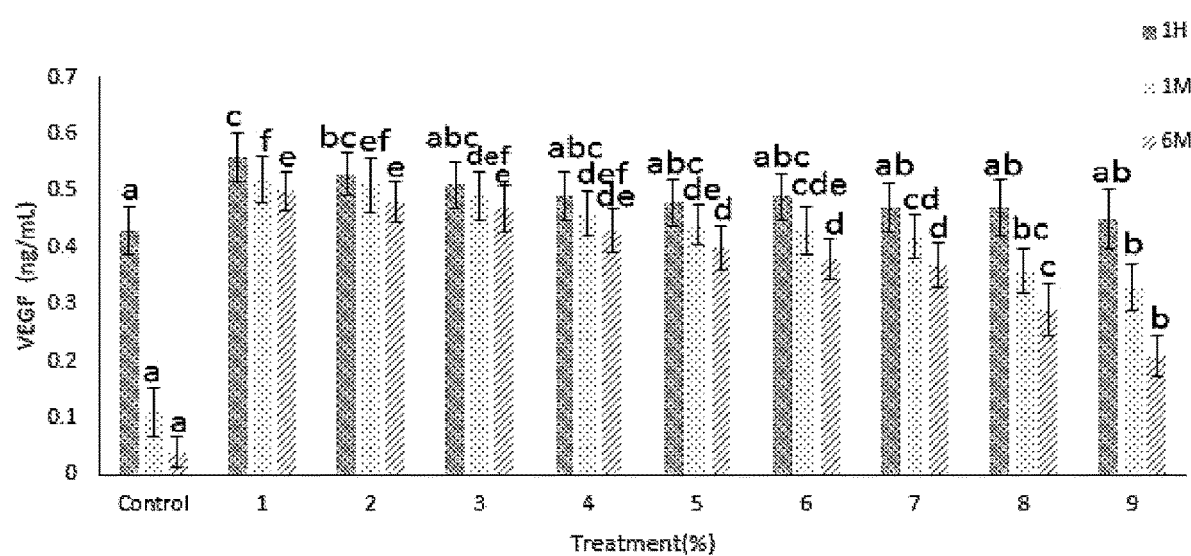

All tests were repeated three times, and the results were analyzed by one-way ANOVA, F-test and Duncan test by SPSS22 software, and expressed as Means±SD. Means in the same bar stripe of storage time with different letters are significantly different (P<0.05). The results are shown in FIGS. 1A-15C.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for blood plasma fibrinogen activity preservation for up to six months, comprising: mixing blood plasma with a combination of protectants to obtain a mixture; and lyophilizing the mixture, wherein the combination of protectants is selected from the group consisting of:
    (a) a combination consisting of 1% triglyceride, 1.6% glycerol, and 0.8% propylene glycol;
    (b) a combination consisting of 0.4% triglyceride, 4% glycerol, and 0.8% dextran;
    (c) a combination consisting of 0.1% triglyceride, 4% glycerol, and 2% sucrose;
    (d) a combination consisting of 0.04% triglyceride, 0.08% glycerol, and 4% albumin;
    (e) a combination consisting of 0.01% triglyceride, 4% dextran, and 0.8% albumin;
    (f) a combination consisting of 4% glutamic acid, 2% propylene glycol, and 0.04% dextran;
    (g) a combination consisting of 1% glutamic acid, 4% albumin, and 0.8% dextran; and
    (h) a combination consisting of 0.4% glutamic acid, 0.4% albumin, and 4% gelatin.

* * * * *